(12) United States Patent
Shenoy et al.

(10) Patent No.: US 6,248,771 B1
(45) Date of Patent: Jun. 19, 2001

(54) FORMULATIONS FOR HYDROPHOBIC PHARMACEUTICAL AGENTS

(75) Inventors: Narmada Shenoy, Sunnyvale; Gregory S. Wagner, Foster City, both of CA (US)

(73) Assignee: Sugen, Inc., Redwood City, CA (US)

( * ) Notice: Subject to any disclaimer, the term of this patent is extended or adjusted under 35 U.S.C. 154(b) by 0 days.

(21) Appl. No.: 09/034,374

(22) Filed: Mar. 4, 1998

Related U.S. Application Data

(60) Provisional application No. 60/039,870, filed on Mar. 5, 1997, and provisional application No. 60/041,251, filed on Mar. 18, 1997.

(51) Int. Cl.⁷ ............................ A01N 43/38; A61K 31/40
(52) U.S. Cl. ........................... 514/418; 548/484; 548/486
(58) Field of Search ............................ 514/418; 548/484, 548/486

(56) References Cited

U.S. PATENT DOCUMENTS

| | | | |
|---|---|---|---|
| Re. 36,256 | 7/1999 | Spada et al. ........................... | 514/249 |
| 3,850,939 | 11/1974 | Elslager et al. . | |
| 3,970,725 | 7/1976 | Tugukuni et al. . | |
| 4,992,271 | 2/1991 | Fernandes et al. . | |
| 5,198,333 | 3/1993 | Dewanckele et al. . | |
| 5,314,685 | 5/1994 | Tyle et al. . | |
| 5,468,898 | 11/1995 | Huang et al. ........................... | 560/41 |

FOREIGN PATENT DOCUMENTS

| | | |
|---|---|---|
| 95/07696 | 3/1995 | (WO) . |
| 95/15758 | 6/1995 | (WO) . |
| 95/24190 | 9/1995 | (WO) . |
| 96/22976 | 8/1996 | (WO) . |
| 96/33745 | 10/1996 | (WO) . |
| 96/39143 | 12/1996 | (WO) . |
| 96/40113 | 12/1996 | (WO) . |
| 96/40116 | 12/1996 | (WO) . |
| 96/40648 | 12/1996 | (WO) . |
| 99/10325 | 4/1999 | (WO) . |

OTHER PUBLICATIONS

Andrews et al. (American Veterinary Medicine Association Panel on Euthanasia), "1993 Report of the AVMA Panel on Euthanasia," *J. American Veterinary Medicine Association* 202(2):229–249 (1993.

Charman et al., "Self–Emulsifying Drug Delivery Systems: Formulation and Biopharmaceutic Evaluation of an Investigational Lipophilic Compound," *Pharmaceutical Research* 9(1):87–93 (1992).

Constantinides, "Lipid Microemulsions for Improving Drug Dissolution and Oral Absorption: Physical and Biopharmaceutical Aspects," *Pharmaceutical Research* 12(11):1561–1572 (1995).

Darnell et al., "Jak–STAT Pathways and Transcriptional Activation in Response to IFNs and Other Extracellular Signaling Proteins," *Science* 264:1415–1421 (1994).

Fischer et al., "Protein Tyrosine Phosphatases: A Diverse Family of Intracellular and Transmembrane Enzymes," *Science* 253:401–406 (1991).

Folkman, "What is the Evidence that Tumors are Angiogenesis Dependent?" *Journal of the National Cancer Institute* 82:4–6 (1990).

Heldin, "Dimerization of Cell Surface Receptors in Signal Transduction," *Cell* 80:213–223 (1995).

Hunter, "Protein–Tyrosine Phosphatases: The Other Side of the Coin," *Cell* 58:1013–1016 (1989).

Hynes et al., "Further Studies on the Synthesis of Quinazolines from 2–Fluorobenzonitriles," *J. Heterocyclic. Chem* 28:1357–1363 (1991).

Hynes et al., "Direct Synthesis of 2,4–Diaminoquinazolines from 2–Fluorobenzonitriles," *J. Heterocyclic. Chem.* 25:1173–1177 (1988).

Klagsbrun and Soker, "VEGF/VPF: the angiogenesis factor found?" *Current Biology* 3:699–702 (1993).

Pawson, "Protein modules and signalling networks," *Nature* 373:573–580 (1995).

Plate et al., "Vascular endothelial growth factor is potential tumor angiogenesis factor in human gilomas in vivo," *Nature* 359:845–848 (1992).

Pot and Dixon, "A thousand and two protein tyrosine phosphates," *Biochem. Biophys. Acta* 1136:35–43 (1992).

Pouton et al., "Self–emulsifying drug delivery systems: assessment of the efficiency of emulsification," *Intl. J. of Pharm.* 27:335–348 (1985).

Saito and Streuli, "Molecular Characterization of Protein Tyrosine Phosphatases," *Cell Growth & Differentation* 2:59–65 (1991).

Schlessinger and Ullrich, "Growth Factor Signalling by Receptor Tyrosine Kinases," *Neuron* 9:383–391 (1992).

Taylor et al., "Structural Framework for the Protein Kinase Family," *Ann. Rev. Cell Biol.* 8:429–462 (1992).

Patent Abstracts of Japan, vol. 010, No. 373: JP 61 167616 A (Nippon Shokubai Kagaku Kogyo Co. Ltd.) Jul. 29, 1986.

Patent Abstracts of Japan, vol. 009, No. 052: JP 59 190967 A (Hokuriku Seiyaku Co. Ltd.) Oct. 29, 1994.

*Primary Examiner*—Gollamudi S. Kishore
(74) *Attorney, Agent, or Firm*—Foley & Lardner

(57) ABSTRACT

The present invention features formulations, including liquid, semi-solid or solid pharmaceutical formulations, that improve the oral bioavailability of hydrophobic pharmaceutical agents, such as quinazoline-, nitrothiazole-, and indolinone-based compounds. Also featured are formulations for parenteral delivery of such hydrophobic pharmaceutical agents, as well as methods of making and using both types of formulations.

25 Claims, 4 Drawing Sheets

Figure 1A

Formulations for Oral Bioavaliability Studies

| Formulation | Formulation Compsition (% w/w) | |
|---|---|---|
| A-05416AD (IV formulation) | Indolinone*<br>Polyethylene Glycol 400<br>Benzyl Alcohol<br>12-Hydroxystearic Acid-PEG<br>Dehydrated Alcohol | 0.6<br>45.0<br>2.0<br>31.5<br>QS |
| 980-4 (Control) | Indolinone<br>Benzyl Alcohol<br>Polysorbate 80<br>NaCl<br>Carboxyl methyl cellulose<br>Water | 3<br>0.9<br>0.4<br>0.9<br>0.5<br>QS |
| F-042-002 (Control) | Indolinone Drug Substance<br>Lactose 316 | 10<br>90 |
| 698-99 | Indolinone<br>Labrasol<br>Polyethylene Glycol 400<br>Cremophor, EL | X[a]<br>76.0<br>12.0<br>12.0 |
| 898-52 | Indolinone<br>Polyethylene Glycol 600<br>Gelucire 44/14<br>Miglyol 812<br>Cremophor, EL 10 | 3.0<br>10<br>70<br>10<br>10 |
| F-042-007 | Indolinone Drug Substance<br>Lactose 316 | 25<br>75 |
| 841-25 (biphasic) | 25:75<br>formulation 841-24 :formulation 898 -52 | |
| 841-28 | Indolinone<br>Polyethylene Glycol 600<br>Gelucire 44/14<br>Miglyol 812<br>Polysorbate-80<br>Na-Taurocholate<br>Lecithin | 2.85<br>10<br>60<br>20<br>8.01<br>0.25<br>7.23 |
| F-042-010 | Indolinone<br>PEG 4500<br>Na-Lauryl sulfate | 32.68<br>65.36<br>1.96 |
| F-042-011 | Indolinone<br>Transcutol<br>Polysorbate-80<br>Cabosil | 4.46<br>89.29<br>1.79<br>4.46 |
| F-042-012 | Indolinone<br>Mineral oil<br>Lecithin<br>Polysorbate-80 | 4.46<br>81.97<br>12.30<br>1.64 |
| 1035-001 | Indolinone<br>Polyethylene Glycol 600<br>Gelucire 50/13<br>Miglyol 812<br>Cremophor, EL | 3.0<br>10<br>70<br>10<br>10 |

Figure 1B

| Formulation | Formulation Compsition (% w/w) | |
|---|---|---|
| 1035-002 | Indolinone | 3.0 |
| | Polyethylene Glycol 600 | 10 |
| | Gelucire 44/14 | 65 |
| | Miglyol 812 | 10 |
| | Cremophor, EL | 10 |
| | Oleic Acid | 5.0 |
| 1035-007 | Indolinone | 3.0 |
| | Lecithin | 5.0 |
| | Gelucire 44/14 | 60 |
| | Miglyol 812 | 10 |
| | Cremophor, EL | 15 |
| | Alcohol | 10 |
| 1035-008 | Indolinone | 3.0 |
| | Polyethylene Glycol 600 | 10 |
| | Gelucire 44/14 | 70 |
| | Cremophor, EL | 10 |
| | capmul | 10 |
| 1035-035 | Indolinone | 3.0 |
| | Gelucire 44/14 | 50 |
| | Capmul | 25 |
| | Cremophor, EL | 25 |
| 1035-036 | Indolinone | 3.0 |
| | Gelucire 44/14 | 50 |
| | Miglyol 812 | 20 |
| | Cremophor, EL | 20 |
| | PVP | 10 |
| 1035-037 | Indolinone | 3.0 |
| | Gelucire 50/13 | 25 |
| | Gelucire 44/14 | 25 |
| | Miglyol 812 | 20 |
| | Cremophor EL | 25 |
| | Triacetin | 5 |
| 980-33 | Indolinone | 3.0 |
| | Polyethylene Glycol 600 | 10 |
| | Labrasol | 70 |
| | Miglyol 812 | 10 |
| | Cremophor, EL | 10 |

*Percent 3-[(2,4-dimethylpyrrol-5-yl)methylene]-2-indolinone added to 100 gm of formulation.

Figure 2A

Summary Of Dosing Regimen And Bioavaliability Study Details

| Cycle: | Formulation Number | Lot No. | Dosage Route | Dosage (mg/kg) | Dog Group | Formulation Conc (mg/mL) |
|---|---|---|---|---|---|---|
| 1 | 698-99 | 898-25 | Oral (PO) | 50 mg/kg | 2 | 31.0 mg/mL |
|  | 698-99 | 898-26 | Oral (PO) | 25 mg/kg | 1 | 15.15 mg/mL |
|  | 698-99 | 898-27 | Oral (PO) | 12.5 mg/kg | 3 | 7.58 mg/mL |
|  | 698-99 | 980-3 | Oral (PO) |  |  | 30 mg/mL |
|  | A-05416AD | 898-28 | IV (Solutol) | 2 mg/kg | 4 | 6 mg/mL |
| 2 | A-05416AD | 898-28 | IV (Solutol) | 2 mg/kg | 1 | 6 mg/mL |
|  | A-05416AD | 898-44 | IV (Solutol) | 1 mg/kg | 2, 3 | 6 mg/mL |
|  | 698-99 | 898-26 | Oral (PO) | 6.25 mg/kg | 4 | 30 mg/mL |
| 3 | 698-99 | 980-3 | Oral (PO) | 50 mg/kg | 2 | 30 mg/mL |
|  | 898-52 | 898-52 | Oral (PO) | 50 mg/kg | 1 | 30 mg/mL |
|  | 980-4 | 980-4 | Oral (PO) Control | 50 mg/kg | 3 | 30 mg/mL |
|  | BA# F-042-007 (Control) | PII | Oral (PO) Capsule | 50mg/kg | 4 | 10% w/w |
| 4 | BA# F-042-002 | PII Form | Oral (PO) | 50 mg/kg | 4 | 10% w/w |
|  | BA# F-042-007 | PII Control | Oral (PO) | 50 mg/kg | 3 | 10% w/w |
| 5 | 898-52 | 898-52 | Oral (PO) | 50 mg/kg | 2 | 30 mg/mL |
| 6 | 898-52 | 898-52 | Oral (PO) | 15 mg/kg | 2 | 30 mg/mL |
| 7 | 841-25 | 841-25 | Oral (PO) | 50 mg/kg | 2 (Dogs 4,6) | 30 mg/mL |
| 8 | 841-28 | 841-28 | Oral (PO) | 50 mg/kg | 2 (Dogs 4,6) | 28.5 mg/mL |
|  | BA# F-042-010 | PII Form | Oral (PO) | 50 mg/kg | 4 (All Dogs) | 33% (w/w) |
|  | BA# F-042-011 | PII Form | Oral (PO) | 50 mg/kg | 3 (Dogs 7,9) | 45% (w/w) |
|  | BA# F-042-012 | PII Form | Oral (PO) | 50 mg/kg | 1 (Dogs 1,2) | 45% (w/w) |
| 9 | 1035-001 | 1035-001 | Oral (PO) | 50 mg/kg | 3 (Dogs 7,9) | 30 mg/mL |
|  | 1035-002 | 1035-002 | Oral (PO) | 50 mg/kg | 4 (All Dogs) | 30 mg/mL |
| 10 | 1035-007 | 1035-007 | Oral (PO) | 50 mg/kg | 3 (Dogs 7,9) | 30 mg/mL |
|  | 1035-008 | 1035-008 | Oral (PO) | 50 mg/kg | 4 (All Dogs) | 30 mg/mL |
| 11 | 1035-013 | 1035-013 | Oral (PO) | 50 mg/kg | 1 (Dogs 1,2) | 30 mg/mL |
|  | 1035-013 | 1035-013 | Oral (PO) | 100 mg/kg | 2 (Dogs 4,6) | 30 mg/mL |
|  | 841-30 | 841-30 | IM | 50 mg/kg | 5 Dogs (3,5) | 194 mg/mL |
| 12 | 980-33 | 980-33 | Oral (PO) | 50 mg/kg | 1 (Dogs 1,2) | 30 mg/mL |
|  | 1035-035 | 1035-035 | Oral (PO) | 50 mg/kg | 2 (Dogs 4,6) | 30 mg/mL |
|  | 1035-036 | 1035-036 | Oral (PO) | 50 mg/kg | 3 (Dogs 7,9) | 30 mg/mL |
|  | 1035-037 | 1035-037 | Oral (PO) | 50 mg/kg | 4 (All Dogs) | 30 mg/mL |
|  |  |  |  |  |  |  |

Figure 2B

| Cycle: | Formulation Number | Lot No. | Dosage Route | Dosage (mg/kg) | Dog Group | Formulation Conc (mg/mL) |
|---|---|---|---|---|---|---|
| 13 | 898-52 | 1035-049 | Oral (PO) | 50 mg/kg | (Dogs 4,6, 10,11) | 30 mg/mL |
|  | 898-52 | 1035-050 | Oral (PO) | 15 mg/kg | (Dogs 1,2,7 9,12) | 9 mg/mL |
| 14 | 898-52 | 1035-058 | Oral (PO) Fed Dogs | 50 mg/kg | (Dogs1,2,3,4,5, and 6) | 30 mg/mL |
|  | A-05416AD | 1035-059 | Oral (PO) | 2 mg/kg | (Dogs 10,11, 12) | 6 mg/mL |
| 15 | 898-52 | 1035-061 | Oral (PO) | 100 mg/kg | (Dogs 4,6, 7, 9, 10, 11, and 12) | 30 mg/mL |
|  | A-05416AD | 1035-059 | Oral (PO) | 2 mg/kg | (Dogs 1,2,3 ) | 6 mg/mL |

FORMULATIONS FOR HYDROPHOBIC PHARMACEUTICAL AGENTS

STATEMENT OF RELATED APPLICATIONS

This application is related to U.S. patent application Ser. No. 60/041,251, filed Mar. 18, 1997 and U.S. patent application Ser. No. 60/039,870, filed Mar. 5, 1997, both of which are incorporated herein by reference in their entirety, including any drawings.

FIELD OF THE INVENTION

The present invention provides liquid, semi-solid or solid pharmaceutical formulations that improve the oral bioavailability of hydrophobic pharmaceutical agents, such as indolinone-, quinazoline-, and nitrothiazole-based compounds. Also provided are formulations for parenteral delivery of such hydrophobic pharmaceutical agents, as well as methods of making and using both types of formulations.

BACKGROUND OF THE INVENTION

The following description of the background of the invention is provided to aid in understanding the invention, but is not admitted to describe or constitute prior art to the invention.

Various methods are available for administering therapeutic agents to a patient. Such methods include, parenteral, oral, ocular, nasal, topical, and transmucosal administration. Variations of these different types of administrations exist. For example, parenteral administration includes intravenous, subcutaneous, intraperitoneal, intramuscular, and intramedullary injection. The chosen mode of administration should take into account the nature of the therapeutic compound and the illness being treated.

Certain potential pharmaceuticals are hydrophobic and typically have very low aqueous solubility and hence low oral bioavailability. Different techniques concerned with solubilizing hydrophobic compounds include those described by Praveen et al., U.S. Pat. No. 5,314,685, and Fernandes et al., U.S. Pat. No. 4,992,271, both of which are incorporated by reference herein in their entirety including any figures and drawings.

One measure of the potential usefulness of an oral formulation of a new pharmaceutical agent is the bioavailability observed after oral administration of the formulation. Various factors can affect the oral bioavailability of the drug. These factors include aqueous solubility, drug absorption throughout the gastrointestinal tract, dosage strength, and first pass effect. Aqueous solubility is one of the most important factors. The oral bioavailability of an aqueous solution formulation of a drug is generally used as the standard or the ideal bioavailability against which other oral formulations are measured. Formulations of drugs that increase the relative bioavailability of the drug as compared to an aqueous solution are desirable, especially with hydrophobic compounds.

SUMMARY OF THE INVENTION

The present invention features formulations (including formulations for oral administration as well as parenteral administration) for hydrophobic pharmaceutical agents, such as indolinone-, quinazoline-, or nitrothiazole-based compounds. Such formulations have advantageous solubility characteristics which allow for administration of hydrophobic pharmaceutical agents, such as indolinone-, quinazoline-, or nitrothiazole-based compounds, for pharmaceutical testing and therapy. Not only do such formulations overcome the solubility problems that have previously plagued the art, they have also been shown to produce a therapeutic effect in test animals.

Thus, a first aspect of the present invention features a formulation comprising: (a) one or more hydrophobic pharmaceutical agents, where the agents are independently selected from the group consisting of quinazoline-, nitrothiazole-, and indolinone-based compounds; (b) one or more polyoxyhydrocarbyl compounds; and (c) one or more pharmaceutically acceptable surfactants.

It is anticipated that the one or more hydrophobic pharmaceutical agents may include a combination of nitrothiazole-based compounds with quinazoline-based compounds, or nitrothiazole-based compounds with indolinone-based compounds, or quinazoline-based compounds with indolinone-based compounds. In addition, the one or more hydrophobic pharmaceutical agents may include a combination of indolinone-based compounds, for example 3-[(2,4-dimethylpyrrol-5-yl)methylene]-(5-amino)-2-indolinone, 3-[(2,4-dimethylpyrrol-5-yl)methylene]-(5-chloro)-2-indolinone, 3-[(2,4-dimethylpyrrol-5-yl)methylene]-2-indolinone, and 3-[(3-methylthiophenyl-5-yl)methylene]-(4-methyl)-2-indolinone. Another possiblity is that the one or more hydrophobic pharmaceutical agents may include a combination of quinazoline-based compounds, for example 4-(3-bromophenyl)-6,7-dimethoxyquinazoline and 4-(3-chlorophenyl)-6,7-dimethoxyquinazoline. Or alternatively, the one or more hydrophobic pharmaceutical agents may include a combination of nitrothiazole-based compounds, for example some combination of 2-methyl-5-[(5-nitrothiazol-2-yl)mercapto]-1,3,4-thiadiazole; 1-benzyl-5-[(5-nitrothiazol-2-yl)mercapto]tetrazole; 2-[(5-nitrothiazol-2-yl)mercapto]-5-t-butyl-1,2,4-triazole; 3-[(5-nitrothiazol-2-yl)mercapto]-5-(thien-2-yl)-1,2,4-triazole; 3-[(5-nitrothiazol-2-yl)mercapto]-5-phenyl-1,2,4-triazole; and 4-allyl-3-hydroxy-5-[(5-nitrothiazole-2-yl)mercapto]-1,2,4-triazole.

The term "hydrophobic pharmaceutical agent" as used herein refers to compounds having a greater solubility in organic solvents of low polarity, such as long chain alcohols, than in aqueous solution. "Hydrophobic" means "water-hating" and is used herein to indicate weakly soluble in water and soluble in non-polar solvents. The formulations described by the present invention facilitate solubilization of hydrophobic compounds which readily dissolve in alcohols. Preferably, the hydrophobic compound is insoluble in aqueous solution. More preferably, the compound has similar solubility characteristics in alcohols and aqueous solution to quinazoline-, nitrothiazole-, and indolinone-based compounds.

The term "compound" refers to the compound or a pharmaceutically acceptable salt, ester, amide, prodrug, isomer, or metabolite, thereof.

The term "pharmaceutically acceptable salt" refers to a formulation of a compound that does not abrogate the biological activity and properties of the compound. Pharmaceutical salts can be obtained by reacting a compound of the invention with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like, or with inorganic or organic bases such as sodium hydroxide, potassium hydroxide, ammonium hydroxide, calcium hydroxide, choline, n-methyl glucamine, diethylamine, procaine and the like.

The term "prodrug" refers to an agent that is converted into the parent drug in vivo. Prodrugs may be easier to administer than the parent drug in some situations. For example, the prodrug may be bioavailable by oral administration but the parent is not, or the prodrug may improve solubility to allow for intravenous administration.

The term "polarity" as used herein refers to the dipole of a molecule. A "dipole" is two equal and opposite charges separated in space. A molecule is polar if it has a dipole, i.e. if the center of negative charge does not coincide with the center of positive charge. The dipole moment of a molecule, is equal to the magnitude of the charge multiplied by the distance between the centers of charge. It is possible to measure the dipole moments of molecules by methods well-known in the art. A low dipole moment indicates low polarity.

The term "quinazoline-based compound" refers to a quinazoline organic compound substituted with chemical substituents. Quinazoline compounds are of the general structure:

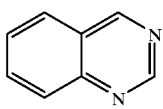

The term "substituted" refers to compounds of the invention that are derivatized with any number of chemical substituents, typically replacing one or more of the hydrogen atoms present in the compound's general structure.

The term "nitrothiazole-based compound" refers to a nitrothiazole organic compound substituted with chemical substituents. Nitrothiazole compounds are of the general structure:

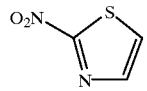

The term "indolinone-based compound" refers to a indolinone organic compound substituted with chemical substituents. Indolinone compounds are of the general structure:

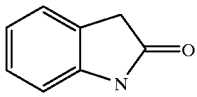

The term "polyoxyhydrocarbyl compound" as used herein refers to a water soluble carbohydrate such as glucose, sucrose, maltotriose, and the like; water soluble carbohydrate derivatives such as gluconic acid and mannitol, and oligosaccharides; and water soluble polymers such as polyvinylpyrrolidone, poly(vinyl alcohol), and in particular, polyethers such as other polyoxyalkylenes including poly (ethylene glycol), or other water soluble mixed oxyalkylene polymers, and the polymeric form of ethylene glycol. Although polyoxyhydrocarbyl compounds preferably contain more than one carbon, oxygen, and hydrogen atom, some molecules such as poly(ethyleneimine) are also included.

A particularly preferred class of solubilizing polyoxyhydrocarbyl moieties comprises poly(ethylene glycol) (PEG) and PEG derivatives, such as PEG monomethyl ether. Other suitable PEG derivatives include PEG-silicon derived ethers. Many of these polymers are commercially available in a variety of molecular weights. Others may be conveniently prepared from commercially available materials, such as by coupling of amino-PEG moiety to a haloalkyl silyl or silane moiety.

Suitable PEGs may vary in molecular weight from about 200 g/mol to about 20,000 g/mol or more, more preferably 200 g/mol to 5,000 g/mol, even more preferably 250 g/mol to 1,000 g/mol, and most preferably 250 g/mol to 500 g/mol. The choice of a particular molecular weight may depend on the particular hydrophobic pharmaceutical agent chosen and its molecular weight and degree of hydrophobicity, as well as the particular application for which the formulation is to be used.

The term "pharmaceutically acceptable surfactant" as used herein refers to a compound that can solubilize hydrophobic compounds into aqueous solutions. Preferably for parenteral formulations, the surfactant is a non-ionic surfactant. Examples of pharmaceutically acceptable surfactants include POLYSORBATE 80® and other polyoxyethylene sorbitan fatty acid esters, glyceryl monooleate, polyvinyl alcohol, ethylene oxide copolymers such as PLURONIC™ (a polyether) and TETRONIC™ (BASF), polyol moieties, and sorbitan esters. Preferably ethoxylated castor oils, such as CREMOPHOR EL®, are used for the formulation of hydrophobic pharmaceutical agents, such as indolinone-, quinazoline-, and nitrothiazole-based compounds.

The term "ethoxylated castor oil" as used herein refers to castor oil that is modified with at least one oxygen containing moiety. In particular the term refers to castor oil comprising at least one ethoxyl moiety.

Further, the term "pharmaceutically acceptable surfactant" as used herein in reference to oral formulations, includes pharmaceutically acceptable non-ionic surfactants (for example polyoxyethylenepolypropylene glycol, such as POLOXAMER® 68 (BASF Corp.) or a mono fatty acid ester of polyoxyethylene (20) sorbitan monooleate (TWEEN® 80), polyoxyethylene (20) sorbitan monostearate (TWEEN® 60), polyoxyethylene (20) sorbitan monopalmitate (TWEEN® 40), polyoxyethylene (20) sorbitan monolaurate (TWEEN® 20) and the like); polyoxyethylene castor oil derivatives (for example, polyoxyethyleneglyceroltriricinoleate or polyoxyl 35 castor oil (CREMOPHOR® EL, BASF Corp.), polyoxyethyleneglycerol oxystearate (CREMOPHOR® RH 40 (polyethyleneglycol 40 hydrogenated castor oil) or CREMOPHOR® RH 60 (polyethyleneglycol 60 hydrogenated castor oil), BASF Corp.) and the like); or a pharmaceutically acceptable anionic surfactant.

The term "pharmaceutically acceptable" or "pharmaceutical" as used herein refers to solutions or components of the formulation that do not prevent the therapeutic compound from exerting a therapeutic effect and do not cause unacceptable adverse side effects. Examples of pharmaceutically acceptable reagents are provided in *The United States Pharmacopeia The National Formulary*, United States Pharmacopeial Convention, Inc., Rockville, Md. 1990 and *FDA Inactive Ingredient Guide* 1990, 1996 issued by the Division of Drug Information Resources (both are hereby incorporated by reference herein, including any drawings). Unacceptable side effects vary for different diseases. Generally, the more severe the disease the more toxic effects which will be tolerated. Unacceptable side effects for different diseases are known in the art.

In preferred embodiments of the invention, the hydrophobic pharmaceutical agent is a quinazoline-based compound of formula I,

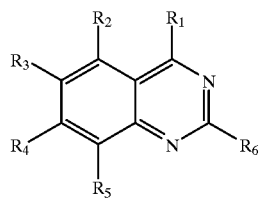

where $R_1$, $R_2$, $R_3$, $R_4$, $R_5$ and $R_6$ are independently selected from the group consisting of: (i) hydrogen; (ii) saturated or unsaturated alkyl; (iii) an aryl optionally substituted with one, two, or three substituents independently selected from the group consisting of alkyl, alkoxy, halogen, trihalomethyl, carboxylate, nitro, and ester moieties; (iv) an amine of formula —$NX_2X_3$, where $X_2$ and $X_3$ are independently selected from the group consisting of hydrogen, saturated or unsaturated alkyl, and homocyclic or heterocyclic ring moieties; (v) halogen or trihalomethyl; (vi) a ketone of formula —CO—$X_4$, where $X_4$ is selected from the group consisting of alkyl and homocyclic or heterocyclic ring moieties; (vii) a carboxylic acid of formula —$(X_5)_n$—COOH or ester of formula —$(X_6)_n$—COO—$X_7$, where $X_5$, $X_6$, and $X_7$ and are independently selected from the group consisting of alkyl and homocyclic or heterocyclic ring moieties and where n is 0 or 1; (viii) an alcohol of formula $(X_8)_n$—OH or an alkoxy moiety of formula —$(X_8)_n$—O—$X_9$, where $X_8$ and $X_9$ are independently selected from the group consisting of saturated or unsaturated alkyl and homocyclic or heterocyclic ring moieties, wherein said ring is optionally substituted with one or more substituents independently selected from the group consisting of alkyl, alkoxy, halogen, trihalomethyl, carboxylate, nitro, and ester and where n is 0 or 1; (ix) an amide of formula —NHCO$X_{10}$, where $X_{10}$ is selected from the group consisting of alkyl, hydroxyl, and homocyclic or heterocyclic ring moieties, wherein said ring is optionally substituted with one or more substituents independently selected from the group consisting of alkyl, alkoxy, halogen, trihalomethyl, carboxylate, nitro, and ester; (x) —$SO_2NX_{11}X_{12}$, where $X_{11}$ and $X_{12}$ are selected from the group consisting of hydrogen, alkyl, and homocyclic or heterocyclic ring moieties; (xi) a homocyclic or heterocyclic ring moiety optionally substituted with one, two, or three substituents independently selected from the group consisting of alkyl, alkoxy, halogen, trihalomethyl, carboxylate, nitro, and ester moieties; (xii) an aldehyde of formula —CO—H; (xiii) a sulfone of formula —$SO_2$—$X_{13}$, where $X_{13}$ is selected from the group consisting of saturated or unsaturated alkyl and homocyclic or heterocyclic ring moieties; and (xiv) a nitro of formula —$NO_2$.

The term "saturated alkyl" refers to an alkyl moiety that does not contain any alkene or alkyne moieties. The alkyl moiety may be branched or non-branched.

The term "unsaturated alkyl" refers to an alkyl moiety that contains at least one alkene or alkyne moiety. The alkyl moiety may be branched or non-branched.

The term "aryl" refers to an aromatic group which has at least one ring having a conjugated pi electron system and includes both carbocyclic aryl (e.g. phenyl) and heterocyclic aryl groups (e.g. pyridine). The term "carbocyclic" refers to a compound which contains one or more covalently closed ring structures, and where the atoms forming the backbone of the ring are all carbon atoms. The term thus distinguishes carbocyclic from "heterocyclic" rings in which the ring backbone contains at least one atom which is different from carbon. The term "heteroaryl" refers to an aryl group which contains at least one heterocyclic ring.

The term "amine" refers to a chemical moiety of formula $NR_1R_2$ where $R_1$ and $R_2$ are independently selected from the group consisting of hydrogen, saturated or unsaturated alkyl, and homocyclic or heterocyclic ring moieties, where the ring is optionally substituted with one or more substituents independently selected from the group consisting of alkyl, halogen, trihalomethyl, carboxylate, nitro, and ester moieties.

The term "halogen" refers to an atom selected from the group consisting of fluorine, chlorine, bromine, and iodine.

The term "ketone" refers to a chemical moiety with formula —$(R)_n$—CO—R', where R and R' are selected from the group consisting of saturated or unsaturated alkyl and homocyclic or heterocyclic ring moieties and where n is 0 or 1.

The term "carboxylic acid" refers to a chemical moiety with formula —$(R)_n$—COOH, where R is selected from the group consisting of saturated or unsaturated alkyl and homocyclic or heterocyclic ring moieties, and where n is 0 or 1.

The term "alcohol" refers to a chemical substituent of formula —ROH, where R is selected from the group consisting of saturated or unsaturated alkyl, and homocyclic or heterocyclic ring moieties, where the ring moiety is optionally substituted with one or more substituents independently selected from the group consisting of alkyl, halogen, trihalomethyl, carboxylate, nitro, and ester moieties.

The term "ester" refers to a chemical moiety with formula —$(R)_n$—COOR', where R and R' are independently selected from the group consisting of saturated or unsaturated alkyl and homocyclic or heterocyclic ring moieties and where n is 0 or 1.

The term "alkoxy" refers to a chemical substituent of formula —OR, where R is hydrogen or a saturated or unsaturated alkyl moiety.

The term "amide" refers to a chemical substituent of formula —NHCOR, where R is selected from the group consisting of hydrogen, alkyl, hydroxyl, and homocyclic or heterocyclic ring moieties, where the ring is optionally substituted with one or more substituents independently selected from the group consisting of alkyl, halogen, trihalomethyl, carboxylate, nitro, or ester.

The term "aldehyde" refers to a chemical moiety with formula —$(R)_n$—CHO, where R is selected from the group consisting of saturated or unsaturated alkyl and homocyclic or heterocyclic ring moieties and where n is 0 or 1.

The term "sulfone" refers to a chemical moiety with formula —$SO_2$—R, where R is selected from the group consisting of saturated or unsaturated alkyl and homocyclic or heterocyclic ring moieties.

In preferred embodiments, the hydrophobic pharmaceutical agent is a quinazoline-based compound of formula II:

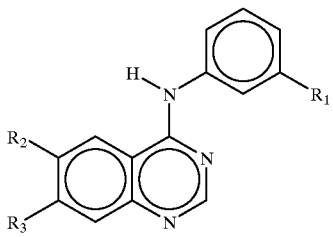

(II)

where $R_1$, $R_2$, and $R_3$ are selected from the group consisting of halogen, trihalomethyl, cyano, methoxy, and hydrogen. Most preferably, the quinazoline-based compound is 4-(3-bromophenyl)-6,7-dimethoxyquinazoline.

In other preferred embodiments of the invention, the hydrophobic pharmaceutical agent is a nitrothiazole-based compound of formula III,

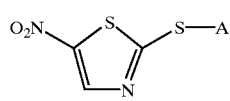

(III)

where A represents (i) a substituted or unsubstituted monocyclic five- or six-membered ring having 1 to 4 hetero ring atoms, at least one of which is nitrogen, the remainder of which are selected from the group consisting of nitrogen, oxygen and sulfur, where examples of such rings include, but are not limited to, pyridine, pyrrole, imidazole, thiazole, isothiazole, isoxazole, furazan, pyrrolidine, piperidine, imidazolidine, piperazine, oxazole, tetrazole, pyrazole, triazole, oxadiazole, thiodiazole; (ii) a substituted or unsubstituted monocyclic or fused bicyclic six- to ten-membered ring having 1 to 4 hetero ring atoms, one of which is nitrogen and the remainder of which are selected from the group consisting of nitrogen, oxygen and sulfur, where such rings include, .but are not limited to, indole, quinoxaline, quinazoline, quinoline, isoquinoline, purine; or (iii) a substituted or unsubstituted monocyclic or fused polycyclic saturated or unsaturated ring having three to 15 atoms, which are selected from the group consisting of carbon, sulfur, nitrogen and oxygen.

The heterocyclic rings defined above may be saturated or unsaturated. The unsaturated rings or heteroaromatic group may, if desired, bear one or more substituents which do not substantially adversely affect the activity of the compound of formula II. Exemplary of such substituents are alkyl, alkoxy, phenoxy, alkenyl, alkynyl, phenylalkyl, hydroxyalkyl, haloalkyl, aryl, arylalkyl, alkyloxy, alkylthio, alkenylthio, phenylalkylthio, hydroxyalkyl-thio, alkylthiocarbamylthio, phenyl, cyclohexyl, pyridyl, piperidinyl, alkylamino, amino, nitro, mercapto, cyano, hydroxyl, a halogen atom, an oxygen atom (forming a ketone or N-oxide) or a sulphur atom (forming a thione).

The terms "alkenyl" and "alkynylu as used herein refer to straight or branched chain hydrocarbon groups having from 2 to 10 carbons and unsaturated by a double or triple bond, respectively, such as vinyl, allyl, propargyl, 1-methylvinyl, but-1-enyl, but-2-enyl, but-2-ynyl, 1 methylbut-2-enyl, pent-1-enyl, pent-3-enyl, 3-methylbut-1-ynyl, 1,1-dimethylallyl, hex-2-enyl and 1-methyl-1-ethylallyl.

The term "phenylalkyl" refers to the aforementioned alkyl groups substituted by a phenyl group. Examples of phenylalkyl groups include, but are not limited to, benzyl, phenethyl, phenopropyl, 1-benzylethyl, phenobutyl and 2-benzylpropyl. The term "hydroxy-alkyl" refers to the aforementioned alkyl groups substituted by a single hydroxyl group. Examples of hydroxyalkyl goups include, but are not limited to, 2-hydroxyethyl, 2-hydroxypropyl, 3-hydroxypropyl, 4-hydroxybutyl, 1-hydroxybutyl and 6-hydroxyhexyl.

The terms "alkylthio, alkenylthio, alkynylthio, alkylthio, hydroxy-alkylthio and phenyl-alkylthio" as used herein refer to the aforementioned alkyl, alkenyl, alkynyl, hydroxy-alkyl and phenyl-alkyl groups linked through a sulfur atom to the compounds of the present invention.

In yet other preferred embodiments, the hydrophobic pharmaceutical agent is a nitrothiazole-based compound of formula IV:

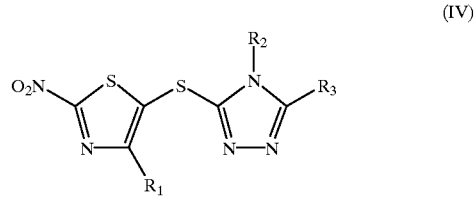

(IV)

where $R_1$, $R_2$, and $R_3$ are independently selected from the group consisting of: (i) hydrogen; (ii) saturated or unsaturated alkyl; (iii) an aryl optionally substituted with one, two, or three substituents independently selected from the group consisting of alkyl, alkoxy, halogen, trihalomethyl, carboxylate, nitro, and ester moieties; (iv) an amine of formula $—NX_2X_3$, where $X_2$ and $X_3$ are independently selected from the group consisting of hydrogen, saturated or unsaturated alkyl, and homocyclic or heterocyclic ring moieties; (v) halogen or trihalomethyl; (vi) a ketone of formula $—CO—X_4$, where $X_4$ is selected from the group consisting of alkyl and homocyclic or heterocyclic ring moieties; (vii) a carboxylic acid of formula $—(X_5)_n—COOH$ or ester of formula $—(X_6)_n—COO—X_7$, where $X_5$, $X_6$, and $X_7$ and are independently selected from the group consisting of alkyl and homocyclic or heterocyclic ring moieties and where n is 0 or 1; (viii) an alcohol of formula $(X_8)_n—OH$ or an alkoxy moiety of formula $—(X_8)_n—O—X_9$, where $X_8$ and $X_9$ are independently selected from the group consisting of saturated or unsaturated alkyl and homocyclic or heterocyclic ring moieties, wherein said ring is optionally substituted with one or more substituents independently selected from the group consisting of alkyl, alkoxy, halogen, trihalomethyl, carboxylate, nitro, and ester and where n is 0 or 1; (ix) an amide of formula $—NHCOX_{10}$, where $X_{10}$ is selected from the group consisting of alkyl, hydroxyl, and homocyclic or heterocyclic ring moieties, wherein said ring is optionally substituted with one or more substituents independently selected from the group consisting of alkyl, alkoxy, halogen, trihalomethyl, carboxylate, nitro, and ester; (x) $—SO_2NX_{11}X_{12}$, where $X_{11}$ and $X_{12}$ are selected from the group consisting of hydrogen, alkyl, and homocyclic or heterocyclic ring moieties; (xi) a homocyclic or heterocyclic ring moiety optionally substituted with one, two, or three substituents independently selected from the group consisting of alkyl, alkoxy, halogen, trihalomethyl, carboxylate, nitro, and ester moieties; (xii) an aldehyde of formula —CO—H; (xiii) a sulfone of formula —SO$_2$—X$_{13}$, where X$_{13}$ is selected from the group consisting of saturated or unsaturated alkyl and homocyclic or heterocyclic ring moieties; and (xiv) a nitro of formula —NO$_2$.

In yet other preferred embodiments of the invention, the hydrophobic pharmaceutical agent is a nitrothiazole-based compound of formula V:

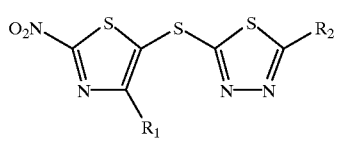

(V)

or a pharmaceutically acceptable salt thereof, wherein R$_1$ and R$_2$ are independently selected from the group consisting of: (i) hydrogen; (ii) saturated or unsaturated alkyl; (iii) an aryl optionally substituted with one, two, or three substituents independently selected from the group consisting of alkyl, alkoxy, halogen, trihalomethyl, carboxylate, nitro, and ester moieties; (iv) an amine of formula —NX$_2$X$_3$, where X$_2$ and X$_3$ are independently selected from the group consisting of hydrogen, saturated or unsaturated alkyl, and homocyclic or heterocyclic ring moieties; (v) halogen or trihalomethyl; (vi) a ketone of formula —CO—X$_4$, where X$_4$ is selected from the group consisting of alkyl and homocyclic or heterocyclic ring moieties; (vii) a carboxylic acid of formula —(X$_5$)$_n$—COOH or ester of formula —(X$_6$)$_n$—COO—X$_7$, where X$_5$, X$_6$, and X$_7$ and are independently selected from the group consisting of alkyl and homocyclic or heterocyclic ring moieties and where n is 0 or 1; (viii) an alcohol of formula (X$_8$)$_n$—OH or an alkoxy moiety of formula —(X$_8$)$_n$—O—X$_9$, where X$_8$ and X$_9$ are independently selected from the group consisting of saturated or unsaturated alkyl and homocyclic or heterocyclic ring moieties, wherein said ring is optionally substituted with one or more substituents independently selected from the group consisting of alkyl, alkoxy, halogen, trihalomethyl, carboxylate, nitro, and ester and where n is 0 or 1; (ix) an amide of formula —NHCOX$_{10}$, where X$_{10}$ selected from the group consisting of alkyl, hydroxyl, and homocyclic or heterocyclic ring moieties, wherein said ring is optionally substituted with one or more substituents independently selected from the group consisting of alkyl, alkoxy, halogen, trihalomethyl, carboxylate, nitro, and ester; (x) —SO$_2$NX$_{11}$X$_{12}$, where X$_{11}$ and X$_{12}$ are selected from the group consisting of hydrogen, alkyl, and homocyclic or heterocyclic ring moieties; (xi) a homocyclic or heterocyclic ring moiety optionally substituted with one, two, or three substituents independently selected from the group consisting of alkyl, alkoxy, halogen, trihalomethyl, carboxylate, nitro, and ester moieties; (xii) an aldehyde of formula —CO—H; (xiii) a sulfone of formula —SO$_2$—X$_{13}$, where X$_{13}$ is selected from the group consisting of saturated or unsaturated alkyl and homocyclic or heterocyclic ring moieties; and (xiv) a nitro of formula —NO$_2$.

In particularly preferred embodiments, the nitrothiazole-based compound is selected from the group consisting of: 2-methyl-5-[(5-nitrothiazol-2-yl)mercapto]-1,3,4-thiadiazole; 1-benzyl-5-[(5-nitrothiazol-2-yl)mercapto] tetrazole; 2-[(5-nitrothiazol-2-yl)mercapto]-5-t-butyl-1,2,4-triazole; 3-[(5-nitrothiazol-2-yl)mercapto]-5-(thien-2-yl)-1,2,4-triazole; 3-[(5-nitrothiazol-2-yl)mercapto]-5-phenyl-1,2,4-triazole; and 4-allyl-3-hydroxy-5-[(5-nitrothiazole-2-yl)mercapto]-1,2,4-triazole.

In yet other preferred embodiments of the invention, the hydrophobic pharmaceutical agent is a indolinone-based compound of formula VI:

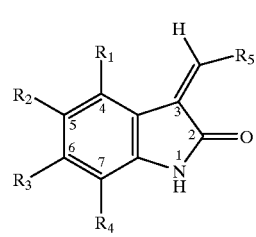

(VI)

where R$_1$, R$_2$, R$_3$, and R$_4$ are selected from the group consisting of hydrogen, trihalomethyl, hydroxyl, amine, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and R$_5$ is an optionally substituted aryl or heteroaryl cyclic moiety.

Preferably, the indolinone-based compound has a structure of formula VI, where R$_1$, R$_2$, R$_3$, and R$_4$ are selected from the group consisting of hydrogen, halogen, alkyl, and alkoxy; and where R$_5$ is a pyrrolyl or thiophenyl moiety optionally substituted with moieties selected from the group consisting of hydrogen, halogen, alkyl, and alkoxy.

More preferably, the indolinone-based compound is selected from the group consisting of 3-[(2,4-dimethylpyrrol-5-yl)methylene]-(5-amino)-2-indolinone, 3-[(2,4-dimethylpyrrol-5-yl)methylene]-(5-chloro)-2-indolinone, 3-[(2,4-dimethylpyrrol-5-yl)methylene]-2-indolinone, and 3-[(3-methylthiophenyl-5-yl)methylene]-(4-methyl)-2-indolinone. Most preferably, the indolinone-based compound is 3-[(2,4-dimethylpyrrol-5-yl)methylene]-2-indolinone.

In some embodiments of the invention, the one or more polyoxyhydrocarbyl compounds are independently selected from the group consisting of: water soluble carbohydrates, water soluble carbohydrate derivatives, polypeptides, water soluble polymers, water soluble mixed oxyalkylene polymers, and the polymeric form of ethylene glycol. Preferably, the one or more polyoxyhydrocarbyl compounds are poly(ethylene glycol) (PEG) or PEG derivatives. More preferably, PEG may vary in molecular weight from about 200 daltons to about 20,000 daltons.

In other embodiments of the invention, the one or more surfactants are one or more non-ionic surfactants. Preferably, the one or more surfactants are independently selected from the group consisting of: polyoxyethylene sorbitan fatty acid esters, glyceryl monooleate, polyvinyl alcohol, ethylene oxide copolymers, polyol moieties, and sorbitan esters. More preferably, the one or more surfactants are one or more ethoxylated castor oils. Most preferably, the ethoxylated castor oil is CREMOPHOR EL®.

In preferred embodiments of the invention the formulation also includes one or more pharmaceutically acceptable alcohols. Preferably, the one or more alcohols are independently selected from the group consisting of ethanol, benzyl alcohol, propylene glycol, 2-(2-ethoxyethoxy)ethanol, and glycerol. Most preferably, the alcohols are ethanol and benzyl alcohol.

The term "pharmaceutically acceptable alcohol" as used herein refers to alcohols which are liquids at about room temperature (approximately 20° C.). These include propylene glycol, ethanol, 2-(2-ethoxyethoxy)ethanol (TRANSCUTOL®, Gattefosse, Westwood, N.J. 07675), benzyl alcohol, and glycerol.

The formulation should be dissolved in a sufficient amount of a pharmaceutically acceptable aqueous solution prior to patient administration to avoid toxic effects due to the alcohol content. The added amount of a pharmaceutically acceptable aqueous solution should be sufficient to avoid hemolysis. Examples of suitable pharmaceutically acceptable aqueous solutions such as WFI (water for injection) and solutions containing isotonic saline are known in the art. Pharmaceutically acceptable aqueous solutions include 0.45% N saline, WFI (water for injection), D5W (5% dextrose in water), and D5W 0.450% N saline.

In other embodiments of the invention, when the hydrophobic pharmaceutical agent is an indolinone-based compound substituted with one or more carboxyl moieties, the formulation further comprises water.

In preferred embodiments of the invention, the formulation comprises (a) 0.1 to 100 mg/mL of an indolinone-based compound of formula VI, where $R_1$, $R_2$, $R_3$, and $R_4$ are selected from the group consisting of hydrogen, trihalomethyl, hydroxyl, amine, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and $R_5$ is an optionally substituted aryl or heteroaryl cyclic moiety; (b) 0.01 to 10 g/mL PEG-400; (c) 0.01 to 1 g/mL ethanol; (d) 0.001 to 1 g/mL benzyl alcohol; and (e) 0.01 to 10 g/mL ethoxylated castor oil.

The term "PEG-400" as used herein refers to a polymeric form of ethylene glycol, polyethylene glycol (PEG), which has an average molecular weight of 400 grams/mole.

In other preferred embodiments the formulation comprises (a) about 5.0 mg/mL of an indolinone-based compound of formula VI, where $R_1$, $R_2$, $R_3$, and $R_4$ are selected from the group consisting of hydrogen, trihalomethyl, hydroxyl, amine, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and $R_5$ is an optionally substituted aryl or heteroaryl cyclic moiety; (b) about 0.35 g/mL PEG-400 (c) about 0.114 g/mL ethanol; (d) about 0.02 g/mL benzyl alcohol; and (e) about 0.25 g/mL CREMOPHOR EL®.

In other preferred embodiments, the invention relates to formulations comprising an indolinone-based compound of formula VI, where $R_1$, $R_2$, $R_3$, and $R_4$ are selected from the group consisting of hydrogen, halogen, alkyl, and alkoxy; and where $R_5$ is a pyrrolyl or thiophenyl moiety optionally substituted with moieties selected from the group consisting of hydrogen, halogen, alkyl, and alkoxy.

In still other preferred embodiments, the invention relates to formulations comprising an indolinone-based compound selected from the group consisting of 3-[(2,4-dimethylpyrrol-5-yl)methylene]-(5-amino)-2-indolinone, 3-[(2,4-dimethylpyrrol-5-yl)methylene]-(5-chloro)-2-indolinone, 3-[(2,4-dimethylpyrrol-5-yl)methylene]-2-indolinone, and 3-[(3-methylthiophenyl-5-yl)methylene]-(4-methyl)-2-indolinone.

A highly preferred embodiment of the invention relates to a formulation comprising about 4.5 mg/mL of the indolinone-based compound, 3-[(2,4-dimethylpyrrol-5-yl) methylene]-2-indolinone, (b) about 45t w/v PEG-400, (c) about 31.5% w/v CREMOPHOR EL®, (d) about 2% w/v benzyl alcohol, and (e) about 9.5% w/v ethanol.

The formulations are stated to comprise the elements described herein, meaning that the formulations can include other components. The solution containing the hydrophobic pharmaceutical agents is preferably adjusted to a pH where the compounds are stable. The pH is preferably adjusted to between 2 and 7. The pH can be adjusted using pharmaceutically acceptable excipients such as ascorbic acid, citric acid, lactic acid, acetic acid, tartaric acid, sodium sulfate, hydrochloric acid, sodium hydroxide, sodium phosphate and sodium acetate. Glycerine can also be added, typically to adjust the isotonicity of a parenteral formulation.

Other components can also be added to the formulations to enhance the therapeutic effects. For example, the hydrophobic pharmaceutical agents may be further formulated in liposomes in addition to the above-mentioned components. Liposomes have been shown to enhance the delivery of compounds into cells by enhancing the compounds' ability to pass through cell plasma membranes to the interior of the cells. However, because the formulations have been shown to have a therapeutic effect with only the components described herein, formulations of the present invention may also "consist essentially of" or "consist of" these components.

In preferred embodiments of the invention, the formulations are effective in treating or preventing an abnormal condition in a patient in need of such treatment. The patient is preferably a mammal and more preferably a human. In a highly preferred embodiment, the formulations are parenteral. Parenteral administration includes intravenous, subcutaneous, intraperitoneal, intramuscular, and intramedullary injection.

The term "preventing" as used herein refers to administering the formulation to a patient before the abnormal condition manifests itself in that patient.

The term "treating" as used herein refers to the method of the invention having a therapeutic effect and at least partially alleviating or abrogating the abnormal condition in the organism.

The term "therapeutic effect" as used herein refers to the inhibition of cell growth causing or contributing to an abnormal condition. The term "therapeutic effect" also refers to the inhibition of factors causing or contributing to the abnormal condition. A therapeutic effect relieves to some extent one or more of the symptoms of the abnormal condition.

The term "mammal" as used herein preferably refers to such organisms as mice, rats, rabbits, guinea pigs, goats, sheep, horses, and cows, for example; more preferably to dogs, cats, monkeys, and apes; and most preferably to humans.

The term "cell proliferative disorder" as used herein refers to a disorder where an excess cell proliferation of one or more subset of cells in a multicellular organism occurs resulting in harm (e.g., discomfort or decreased life expectancy) to the multicellular organism. The excess cell proliferation can be determined by reference to the general population and/or by reference to a particular patient (e.g., at an earlier point in the patient's life). Hyper-proliferative cell disorders can occur in different types of animals and in humans, and produce different physical manifestations depending upon the affected cells. Hyper-proliferative cell disorders include cancers, blood vessel proliferative disorders, fibrotic disorders, and autoimmune disorders.

In reference to the treatment of abnormal cell proliferative conditions, a therapeutic effect refers to one or more of the following: (a) a reduction in tumor size; (b) inhibition (i.e., slowing or stopping) tumor metastasis; (c) inhibition of tumor growth; and (d) relieving to some extent one or more of the symptoms associated with the abnormal condition.

Compounds demonstrating efficacy against leukemias can be identified as described herein, except that rather than inhibiting metastasis, the compounds may instead slow or decrease cell proliferation or cell growth.

The term "abnormal condition" refers to a function in the cells or tissues of a patient that deviates from their normal functions in that patient. An abnormal condition can relate to cell proliferation as described herein.

The present invention also features oral formulations for hydrophobic pharmaceutical agents, such as quinazoline-, nitrothiazole- and indolinone-based compounds. The oral formulations, which include one or more polyoxyhydrocarbyl compounds, one or more polyglycolized lipids, and one or more surfactants, also have advantageous solubility characteristics and oral bioavailability. These formulations allow for the oral administration of the hydrophobic pharmaceutical agents for testing and therapy and have shown efficacy in the preclinical angiogenesis mice model. 3-[(2,4-dimethylpyrrol-5-yl)methylene]-2-indolinone is the most widely tested of Applicant's indolinone-based compounds. The oral formulations of 3-[(2,4-dimethylpyrrol-5-yl) methylene]-2-indolinone have shown therapeutic effect in test animals.

Thus, a featured aspect of the invention is a formulation comprising: (a) one or more hydrophobic pharmaceutical agents, where the agents are independently selected from the group consisting of quinazoline-, nitrothiazole- and indolinone-based compounds; (b) one or more polyoxyhydrocarbyl compounds; (c) one or more polyglycolized lipids; and (d) one or more pharmaceutically acceptable surfactants.

It is anticipated that the one or more hydrophobic pharmaceutical agents may include a combination of nitrothiazole-based compounds with quinazoline-based compounds, or nitrothiazole-based compounds with indolinone-based compounds, or quinazoline-based compounds with indolinone-based compounds. In addition, the one or more hydrophobic pharmaceutical agents may include a combination of indolinone-based compounds, for example 3-[(2,4-dimethylpyrrol-5-yl)methylene]-(5-amino)-2-indolinone, 3-[(2,4-dimethylpyrrol-5-yl) methylene]-(5-chloro)-2-indolinone, 3-[(2,4-dimethylpyrrol-5-yl)methylene]-2-indolinone, and 3-[(3-methylthiophenyl-5-yl)methylene]-(4-methyl)-2-indolinone. Another possiblity is that the one or more hydrophobic pharmaceutical agents may include a combination of quinazoline-based compounds, for example 4-(3-bromophenyl)-6,7-dimethoxyquinazoline and 4-(3-chlorophenyl)-6,7-dimethoxyquinazoline. Or alternatively, the one or more hydrophobic pharmaceutical agents may include a combination of nitrothiazole-based compounds, for example some combination of 2-methyl-5-[(5-nitrothiazol-2-yl)mercapto]-1,3,4-thiadiazole; 1-benzyl-5-[(5-nitrothiazol-2-yl)mercapto]tetrazole; 2-[(5-nitrothiazol-2-yl)mercapto]-5-t-butyl-1,2,4-triazole; 3-[(5-nitrothiazol-2-yl)mercapto]-5-(thien-2-yl)-1,2,4-triazole; 3-[(5-nitrothiazol-2-yl)mercapto]-5-phenyl-1,2,4-triazole; and 4-allyl-3-hydroxy-5-[(5-nitrothiazole-2-yl)mercapto]-1,2,4-triazole.

The term "polyglycolized lipids" as used herein refers to mixtures of monoglycerides, diglycerides, or triglycerides and polyethyleneglycol monoesters and diesters formed by the partial alcoholysis of vegetable oil using PEG of 200 g/mol to 2,000 g/mol or by the esterification of fatty acids using PEG 200 g/mol to 2,000 g/mol and glycerols. Preferably these include GELUCIRE® 35/10, GELUCIRE® 44/14, GELUCIRE® 46/07, GELUCIRE® 50/13, GELUCIRE® 53/10, and LABRASOL®.

In preferred embodiments of the invention, the hydrophobic pharmaceutical agent is a quinazoline-based compound of formula I, where $R_1$, $R_2$, $R_3$, $R_4$, $R_5$ and $R_6$ are independently selected from the group consisting of: (i) hydrogen; (ii)saturated or unsaturated alkyl; (iii) an aryl optionally substituted with one, two, or three substituents independently selected from the group consisting of alkyl, alkoxy, halogen, trihalomethyl, carboxylate, nitro, and ester moieties; (iv) an amine of formula —$NX_2X_3$, where $X_2$ and $X_3$ are independently selected from the group consisting of hydrogen, saturated or unsaturated alkyl, and homocyclic or heterocyclic ring moieties; (v) halogen or trihalomethyl; (vi) a ketone of formula —CO—$X_4$, where $X_4$ is selected from the group consisting of alkyl and homocyclic or heterocyclic ring moieties; (vii) a carboxylic acid of formula —$(X_5)_n$—COOH or ester of formula —$(X_6)_n$—COO—$X_7$, where $X_5$, $X_6$, and $X_7$ and are independently selected from the group consisting of alkyl and homocyclic or heterocyclic ring moieties and where n is 0 or 1; (viii) an alcohol of formula $(X_8)_n$—OH or an alkoxy moiety of formula —$(X_8)_n$—O—$X_9$, where $X_8$ and $X_9$ are independently selected from the group consisting of saturated or unsaturated alkyl and homocyclic or heterocyclic ring moieties, wherein said ring is optionally substituted with one or more substituents independently selected from the group consisting of alkyl, alkoxy; halogen, trihalomethyl, carboxylate, nitro, and ester and where n is 0 or 1; (ix) an amide of formula —$NHCOX_{10}$, where $X_{10}$ is selected from the group consisting of alkyl, hydroxyl, and homocyclic or heterocyclic ring moieties, wherein said ring is optionally substituted with one or more substituents independently selected from the group consisting of alkyl, alkoxy, halogen, trihalomethyl, carboxylate, nitro, and ester; (x) —$SO_2NX_{11}X_{12}$, where $X_{11}$ and $X_{12}$ are selected from the group consisting of hydrogen, alkyl, and homocyclic or heterocyclic ring moieties; (xi) a homocyclic or heterocyclic ring moiety optionally substituted with one, two, or three substituents independently selected from the group consisting of alkyl, alkoxy, halogen, trihalomethyl, carboxylate, nitro, and ester moieties; (xii) an aldehyde of formula —CO—H; and (xiii) a sulfone of formula —$SO_2$—$X_{13}$, where $X_{13}$ is selected from the group consisting of saturated or unsaturated alkyl and homocyclic or heterocyclic ring moieties.

In other preferred embodiments of the invention, the hydrophobic pharmaceutical agent is a quinazoline-based compound of formula II, where $R_1$, $R_2$, and $R_3$ are selected from the group consisting of halogen, trihalomethyl, cyano, methoxy, and hydrogen. Most preferably, the quinazoline-based compound is 4-(3-bromophenyl)-6,7-dimethoxyquinazoline.

In yet other preferred embodiments of the invention, the hydrophobic pharmaceutical agent is a nitrothiazole-based compound of formula IV, wherein $R_1$, $R_2$, and $R_3$ are independently selected from the group consisting of: (i) hydrogen; (ii) saturated or unsaturated alkyl; (iii) an aryl optionally substituted with one, two, or three substituents independently selected from the group consisting of alkyl, alkoxy, halogen, trihalomethyl, carboxylate, nitro, and ester moieties; (iv) an amine of formula —$NX_2X_3$, where $X_2$ and $X_3$ are independently selected from the group consisting of hydrogen, saturated or unsaturated alkyl, and homocyclic or heterocyclic ring moieties; (v) halogen or trihalomethyl; (vi) a ketone of formula —CO—$X_4$, where $X_4$ is selected from the group consisting of alkyl and homocyclic or heterocyclic ring moieties; (vii) a carboxylic acid of formula —$(X_5)_n$—COOH or ester of formula —$(X_6)_n$—COO—$X_7$, where $X_5$, $X_6$, and $X_7$ and are independently selected from the group consisting of alkyl and homocyclic or heterocyclic ring moieties and where n is 0 or 1; (viii) an alcohol of formula $(X_8)_n$—OH or an alkoxy moiety of formula —$(X_8)_n$—O—$X_9$, where $X_8$ and $X_9$ are independently selected from the group consisting of saturated or unsaturated alkyl and homocyclic or heterocyclic ring moieties, wherein said ring is optionally substituted with one or more substituents independently selected from the group consisting of alkyl, alkoxy, halogen, trihalomethyl, carboxylate, nitro, and ester and where n is 0 or 1; (ix) an amide of formula —NHCOX$_{10}$, where $X_{10}$ is selected from the group consisting of alkyl, hydroxyl, and homocyclic or heterocyclic ring moieties, wherein said ring is optionally substituted with one or more substituents independently selected from the group consisting of alkyl, alkoxy, halogen, trihalomethyl, carboxylate, nitro, and ester; (x) —SO$_2$NX$_{11}$X$_{12}$, where $X_{11}$ and $X_{12}$ are selected from the group consisting of hydrogen, alkyl, and homocyclic or heterocyclic ring moieties; (xi) a homocyclic or heterocyclic ring moiety optionally substituted with one, two, or three substituents independently selected from the group consisting of alkyl, alkoxy, halogen, trihalomethyl, carboxylate, nitro, and ester moieties; (xii) an aldehyde of formula —CO—H; and (xiii) a sulfone of formula —SO$_2$—X$_{13}$, where $X_{13}$ is selected from the group consisting of saturated or unsaturated alkyl and homocyclic or heterocyclic ring moieties.

In yet other preferred embodiments of the invention, the hydrophobic pharmaceutical agent is a nitrothiazole-based compound of formula V, wherein $R_1$ and $R_2$ are independently selected from: (i) hydrogen; (ii) saturated or unsaturated alkyl; (iii) an aryl optionally substituted with one, two, or three substituents independently selected from the group consisting of alkyl, alkoxy, halogen, trihalomethyl, carboxylate, nitro, and ester moieties; (iv) an amine of formula —NX$_2$X$_3$, where $X_2$ and $X_3$ are independently selected from the group consisting of hydrogen, saturated or unsaturated alkyl, and homocyclic or heterocyclic ring moieties; (v) halogen or trihalomethyl; (vi) a ketone of formula —CO—X$_4$, where $X_4$ is selected from the group consisting of alkyl and homocyclic or heterocyclic ring moieties; (vii) a carboxylic acid of formula —(X$_5$)$_n$—COOH or ester of formula —(X$_6$)$_n$—COO—X$_7$, where $X_5$, $X_6$, and $X_7$ and are independently selected from the group consisting of alkyl and homocyclic or heterocyclic ring moieties and where n is 0 or 1; (viii) an alcohol of formula $(X_8)_n$—OH or an alkoxy moiety of formula —$(X_8)_n$—O—$X_9$, where $X_8$ and $X_9$ are independently selected from the group consisting of saturated or unsaturated alkyl and homocyclic or heterocyclic ring moieties, wherein said ring is optionally substituted with one or more substituents independently selected from the group consisting of alkyl, alkoxy, halogen, trihalomethyl, carboxylate, nitro, and ester and where n is 0 or 1; (ix) an amide of formula —NHCOX$_{10}$, where $X_{10}$ is selected from the group consisting of alkyl, hydroxyl, and homocyclic or heterocyclic ring moieties, wherein said ring is optionally substituted with one or more substituents independently selected from the group consisting of alkyl, alkoxy, halogen, trihalomethyl, carboxylate, nitro, and ester; (x) —SO$_2$NX$_{11}$X$_{12}$, where $X_{11}$ and $X_{12}$ are selected from the group consisting of hydrogen, alkyl, and homocyclic or heterocyclic ring moieties; (xi) a homocyclic or heterocyclic ring moiety optionally substituted with one, two, or three substituents independently selected from the group consisting of alkyl, alkoxy, halogen, trihalomethyl, carboxylate, nitro, and ester moieties; (xii) an aldehyde of formula —CO—H; and (xiii) a sulfone of formula —SO$_2$—X$_{13}$, where $X_{13}$ is selected from the group consisting of saturated or unsaturated alkyl and homocyclic or heterocyclic ring moieties.

In particularly preferred embodiments of the invention, the nitrothiazole-based compound is selected from the group consisting of: 2-methyl-5-[(5-nitrothiazol-2-yl)mercapto]-1,3,4-thiadole; 1-benzyl-5-[(5-nitrothiazol-2-yl)mercapto]tetrazole; 2-[(5-nitrothiazol-2-yl)mercapto]-5-t-butyl-1,2,4-triazole; 3-[(5-nitrothiazol-2-yl)mercapto]-5-(thien-2-yl)-1,2,4-triazole; 3-[(5-nitrothiazol-2-yl)mercapto]-5-phenyl-1,2,4-triazole; and 4-allyl-3-hydroxy-5-[(5-nitrothiazole-2-yl)mercapto]-1,2,4-triazole.

In other preferred embodiments of the invention, the hydrophobic pharmaceutical agent is an indolinone-based compound of formula VI, where $R_1$, $R_2$, $R_3$, and $R_4$ are selected from the group consisting of hydrogen, trihalomethyl, hydroxyl, amine, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and $R_5$ is an optionally substituted aryl or heteroaryl cyclic moiety.

Preferably, the indolinone-based compound has a structure of formula VI, where $R_1$, $R_2$, $R_3$, and $R_4$ are selected from the group consisting of hydrogen, halogen, alkyl, and alkoxy; and where $R_5$ is a pyrrolyl or thiophenyl moiety optionally substituted with moieties selected from the group consisting of hydrogen, halogen, alkyl, and alkoxy.

More preferably, the indolinone-based compound is selected from the group consisting of 3-[(2,4-dimethylpyrrol-5-yl)methylene]-(5-amino)-2-indolinone, 3-[(2,4-dimethylpyrrol-5-yl)methylene]-(5-chloro)-2-indolinone, 3-[(2,4-dimethylpyrrol-5-yl)methylene]-2-indolinone, and 3-[(3-methylthiophenyl-5-yl)methylene]-(4-methyl)-2-indolinone. Most preferably, the indolinone-based compound is 3-[(2,4-dimethylpyrrol-5-yl)methylene]-2-indolinone.

In some embodiments of the invention, the one or more polyoxyhydrocarbyl compounds are independently selected from the group consisting of: water soluble carbohydrates, water soluble carbohydrate derivatives, polypeptides, water soluble polymers, water soluble mixed oxyalkylene polymers, and the polymeric form of ethylene glycol. Preferably, the one or more polyoxyhydrocarbyl compounds are poly(ethylene glycol) (PEG) or PEG derivatives. More preferably, PEG may vary in molecular weight from about 200 daltons to about 20,000 daltons.

In other embodiments of the invention, the one or more polyglycolized lipids are mixtures of monoglycerides, diglycerides, or triglycerides and polyethyleneglycol monoesters and diesters. Preferably, the one or more polyglycolized lipids are selected from the group consisting of: GELUCIRE® 35/10, GELUCIRE® 44/14, GELUCIRE® 46/07, GELUCIRE® 50/13, GELUCIRE® 53/10, and LABRASOL®. Most preferably, the polyglycolized lipids are selected from the group consisting of GELUCIRE® 44/14 and LABRASOL®.

In other embodiments of the invention, the one or more surfactants are selected independently from the group consisting of pharmaceutically acceptable non-ionic surfactants, polyoxyethylene castor oil derivatives, and pharmaceutically acceptable anionic surfactants. In highly preferred embodiments, the surfactant is CREMOPHOR EL®.

Other preferred embodiments of the invention feature formulations that also contain one or more pharmaceutically acceptable oils selected independently from the group consisting of mineral oil, vegetable oil, fractionated coconut oil, propyleneglycol monolaurate, and mixed triglycerides with caprylic acid and capric acid. In a highly preferred embodiment, the oil is Miglyol 812.

The term "pharmaceutically acceptable oils" as used herein refers to oils such as mineral oil or vegetable oil (including safflower oil, peanut oil, and olive oil), fractionated coconut oil, propyleneglycol monolaurate, mixed triglycerides with caprylic acid and capric acid, and the like. Preferred embodiments of the invention feature mineral oil, vegetable oil, fractionated coconut oil, mixed triglycerides with caprylic acid, and capric acid. A highly preferred embodiment of the invention features Miglyol 812 (available from Huls America, USA).

In yet other preferred embodiments, when the hydrophobic pharmaceutical agent is an indolinone-based compound substituted with one or more carboxyl moieties, the formulation also comprises water.

In other preferred embodiments, the invention relates to formulations comprising: (a) about 3% w/w of an indolinone-based compound of formula VI, where $R_1$, $R_2$, $R_3$, and $R_4$ are selected from the group consisting of hydrogen, trihalomethyl, hydroxyl, amine, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and $R_5$ is an optionally substituted aryl or heteroaryl cyclic moiety; (b) about 70% w/w GELUCIRE® 44/14; (c) about 10% w/w CREMOPHOR EL®; (d) about 10% w/w Miglyol 812; and (e) about 10% w/w polyethylene glycol 600.

In other preferred embodiments, the invention relates to formulations comprising: (a) about 3% w/w of an indolinone-based compound of formula VI, where $R_1$, $R_2$, $R_3$, and $R_4$ are selected from the group consisting of hydrogen, trihalomethyl, hydroxyl, amine, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and $R_5$ is an optionally substituted aryl or heteroaryl cyclic moiety; (b) about 76% w/w LABRASOL"; (c) about 12% w/w CREMOPHOR EL®; and (d) about 12% w/w polyethylene glycol 600.

In other preferred embodiments, the invention relates to formulations comprising: (a) about 3% w/w of an indolinone-based compound of formula VI, where $R_1$, $R_2$, $R_3$, and $R_4$ are selected from the group consisting of hydrogen, trihalomethyl, hydroxyl, amine, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and $R_5$ is an optionally substituted aryl or heteroaryl cyclic moiety; (b) about 70% w/w LABRASOL®; (c) about 10% w/w CREMOPHOR EL®; (d) about 10% w/w Miglyol 812; and (e) about 10% w/w polyethylene glycol 600.

In the most preferred embodiments, these formulations feature 3-[(2,4-dimethylpyrrol-5-yl)methylene]-2-indolinone as the indolinone-based compound.

Preferably, the formulations are effective in treating or preventing an abnormal condition in a patient, preferably a mammal, more preferably a human, in need of such treatment. The formulation is preferably administered orally. Abnormal conditions which may be treated with these formulations include cell proliferative disorders, typically those characterized by abnormal protein kinase activity. Preferably, the formulation inhibits protein kinase activity.

The compositions of the invention can also include from about 0 to about 3 molar equivalents (based on the amount of the indolinone-based compound or other hydrophobic pharmaceutical agent in the composition) of a pharmaceutically acceptable acid or base or a mixture of pharmaceutically acceptable acids or bases. Preferably, the pharmaceutically acceptable acid or base or mixture of pharmaceutically acceptable acids is present in a total amount of from about 0.2 to about 2.0 molar equivalents (based on the amount of the indolinone-based compound or other hydrophobic pharmaceutical agent in the composition).

The solution can also include from about 0% to about 10% (by weight of the total solution) of water, and may also include an antioxidant (for example, ascorbic acid, BHA (butylated hydroxyanisole), BHT (butylated hydroxytoluene), vitamin E, vitamin E PEG 1000 succinate and the like) for chemical stability. Solutions encapsulated in a SEC may also include glycerin for physical stability.

The compositions of this invention (e.g. solution/semisolid or solid or encapsulated solution/semisolid or solid) provide improved oral bioavailability for 3-[(2,4-dimethylpyrrol-5-yl)methylene]-2-indolinone when compared to non-formulated 3-[(2,4-dimethylpyrrol-5-yl) methylene]-2-indolinone.

In another aspect, the invention relates to a method of testing the solubility of hydrophobic pharmaceutical agents in a parenteral formulation comprising one or more hydrophobic pharmaceutical agents, that are independently selected from the group consisting of quinazoline-, nitrothiazole-, and indolinone-based compounds; one or more polyoxyhydrocarbyl compounds; and one or more pharmaceutically acceptable surfactants. The method of testing the solubility of the one or more hydrophobic pharmaceutical agents comprises the following steps: (a) interacting the formulation with a hydrophobic support in a first solvent; (b) eluting the hydrophobic pharmaceutical agent from the support with a second solvent; and (c) comparing the amount of the hydrophobic pharmaceutical agent that elutes from the support to the amount that was added to the formulation.

The term "hydrophobic support" as used herein refers to a solid matrix that comprises hydrocarbon moieties. The solid matrix can include reverse phase silica, cellulose, and others commonly known to those skilled in the art. The hydrocarbon moieties can include preferably about four carbon atoms, more preferably about eight carbon atoms, and most preferably about eighteen carbon atoms. The solid matrix can be contained within a high performance liquid chromatography (HPLC) column. A pump system attached to such a column can deliver solvents to the matrix at high pressures and render high resolution of compounds eluting from the column.

The term "interacting" as used herein with reference to the solid support refers to adsorbing one or more molecules in a formulation to the solid support. Adsorbing or binding the molecules to the solid support can be accomplished in different solvents, preferably those described herein by example.

The term "eluting" as used herein with reference to the solid support refers to the processes of desorbing (removing) a hydrophobic pharmaceutical agent such as an indolinone-, a quinazoline-, or a nitrothiazole-based compound adsorbed (reversibly bound) to a solid support. Eluting a compound from a solid support can be accomplished by changing the solvent to one where the hydrophobic pharmaceutical agent no longer binds to the solid support. The second solvent often has a different pH or a different solvent content than the solvent in which the hydrophobic pharmaceutical agent adsorbed to the solid support. When a HPLC column is employed in this process, a hydrophobic pharmaceutical agent is typically bound to the column in one solvent and then eluted by passing another solvent through the column. The hydrophobic pharmaceutical agent flows from the column with the second solvent.

The term "comparing" as used herein in reference to the method of testing the solubility of the hydrophobic pharmaceutical agent refers to difference in the amount of a hydrophobic pharmaceutical agent added to a formulation and the amount of the hydrophobic pharmaceutical agent that is actually dissolved in the formulation. One may determine the amount of the hydrophobic pharmaceutical agent added to the formulation, for example, by weighing the compound before adding it to the formulation. Then one can centrifuge or filter a sample of the formulation to remove any hydrophobic pharmaceutical agent that is not dissolved in the formulation. The filtered or centrifuged formulation can then be injected onto an HPLC column and eluted from it. The concentration of the hydrophobic pharmaceutical agent can then be quantified by techniques commonly known to those skilled in the art, such as by using a ultraviolet detector which measures the amount of an hydrophobic pharmaceutical agent eluted from the column by its absorbance. The concentration of the hydrophobic pharmaceutical agent eluted from the column can be determined from its absorbance and its inherent extinction coefficient and/or by comparing the absorbance to that of standard amounts of the hydrophobic pharmaceutical agent.

In preferred embodiments of the method of testing the solubility of hydrophobic pharmaceutical agents in a parenteral formulation, the parenteral formulation further comprises one or more pharmaceutically acceptable alcohols.

In another aspect, the invention relates to a method of testing the solubility of hydrophobic pharmaceutical agents in an oral formulation comprising one or more hydrophobic pharmaceutical agents that are independently selected from the group consisting of quinazoline-, nitrothiazole-, and indolinone-based compounds; one or more polyoxyhydrocarbyl compounds; one or more polyglycolized lipids; and one or more pharmaceutically acceptable surfactants. The method of testing the solubility of the one or more hydrophobic pharmaceutical agents comprises the following steps: (a) interacting the formulation with a hydrophobic support in a first solvent; (b) eluting the hydrophobic pharmaceutical agent from the support with a second solvent; and (c) comparing the amount of the hydrophobic pharmaceutical agent that elutes from the support to the amount that was added to the formulation.

In preferred embodiments of the method of testing the solubility of hydrophobic pharmaceutical agents in an oral formulation, the parenteral formulation further comprises one or more pharmaceutically acceptable oils.

In preferred embodiments of the method of testing the solubility of hydrophobic pharmaceutical agents, the first solvent comprises phosphate and triethylamine, and the second solvent comprises triethylamine, tetrahydrofuran, and methanol. Preferably the first solvent comprises 0.35 M phosphate and 0.1% triethylamine and the second solvent comprises 0.1% triethylamine, tetrahydrofuran, and methanol mixed in a 40:20:40 ratio.

Most preferably, the hydrophobic pharmaceutical agent is an indolinone-based compound of formula VI.

In yet another aspect, the invention relates to a method of preparing a parenteral formulation. The method comprises the following steps: (a) dissolving one or more hydrophobic pharmaceutical agents into polyoxyhydrocarbyl compounds to form a solution, where the agents are independently selected from the group consisting of: a quinazoline-, a nitrothiazole-, and an indolinone-based compound; (b) dissolving one or more surfactants into the solution; and (c) filtering the solution. In some embodiments, one or more pharmaceutically acceptable alcohols are added to the solution.

In preferred embodiments, the invention relates to the method of preparing a parenteral formulation comprising the following steps: (a) dissolving 0.01 to 10 g/mL PEG-400 into water; (b) dissolving an indolinone-based compound of formula VI into the solution, where $R_1$, $R_2$, $R_3$, and $R_4$ are selected from the group consisting of hydrogen, trihalomethyl, hydroxyl, amine, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and $R_5$ is an optionally substituted aryl or heteroaryl cyclic moiety; (c) adding 0.01 to 1 g/mL ethanol and 0.001 to 1 g/mL benzyl alcohol to the solution; (d) dissolving 0.01 to 10 g/mL ethoxylated castor oil into the solution; (e) bringing the volume of the solution to about 100 milliliters with distilled water; and (f) filtering the solution through a 0.2 Am nylon filter.

In other preferred embodiments, the invention relates to the method of preparing a parenteral formulation comprising the following steps: (a) dissolving about 35 grams of PEG-400 into water; (b) dissolving about 500 milligrams of an indolinone-based compound of formula VI, where $R_1$, $R_2$, $R_3$, and $R_4$ are selected from the group consisting of hydrogen, trihalomethyl, hydroxyl, amine, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and $R_5$ is an optionally substituted aryl or heteroaryl cyclic moiety; (c) adding about 11.4 grams of ethanol and 2 grams of benzyl alcohol to the solution; (d) dissolving about 25 grams of CREMOPHOR EL® into the solution; (e) bringing the volume of the solution to about 100 milliliters with distilled water; and (f) filtering the solution through a 0.2 $\mu$m nylon filter.

In yet another aspect, the invention relates to a method of preparing an oral formulation comprising the following steps: (a) melting one or more polyglycolyzed lipids;(b) dissolving one or more polyoxyhydrocarbyl compounds and one or more surfactants, into the melted polyglycolyzed lipid; (c) dissolving one or more hydrophobic pharmaceutical agent into the solution, where the agents are independently selected from the group consisting of a quinazoline-, a nitrothiazole-, and an indolinone-based compound; and (d) filtering the solution. In some embodiments, pharmaceutically acceptable oils are also dissolved into the melted polyglycolyzed lipid.

In preferred embodiments of the methods of making the parenteral and oral formulations, the hydrophobic pharmaceutical agent is an indolinone-based compound of formula VI where $R_1$, $R_2$, $R_3$, and $R_4$ are selected from the group consisting of hydrogen, trihalomethyl, hydroxyl, amine, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and $R_5$ is an optionally substituted aryl or heteroaryl cyclic moiety.

Preferably, the indolinone-based compound has a structure of formula VI, where $R_1$, $R_2$, $R_3$, and $R_4$ are selected from the group consisting of hydrogen, halogen, alkyl, and alkoxy; and where $R_5$ is a pyrrolyl or thiophenyl moiety optionally substituted with moieties selected from the group consisting of hydrogen, halogen, alkyl, and alkoxy. More preferably, the indolinone-based compound is selected from the group consisting of 3-[(2,4-dimethylpyrrol-5-yl) methylene]-(5-amino)-2-indolinone, 3-[(2,4-dimethylpyrrol-5-yl)methylene]-(5-chloro)-2-indolinone, 3-[(2,4-dimethylpyrrol-5-yl)methylene]-2-indolinone, and 3-[(3-methylthiophenyl-5-yl)methylene]-(4-methyl)-2-indolinone. In a highly preferred method, the indolinone-based compound is 3-[(2,4-dimethylpyrrol-5-yl)methylene]-2-indolinone.

The methods of preparing formulations of the invention can be scaled to any volume desired. Thus, even if a method specifies that the total volume of the solution is 100 mL, the formulation can be prepared as a 1 mL sample by proportionally decreasing each component of the formulation by a factor of 100. For example, if 10 grams of PEG-400 is required for a 100 mL volume of the formulation, then a 1 mL sample of the formulation can be prepared by adding only (10 grams)×(1/100)=0.1 grams of PEG-400.

Dissolving the components of the formulations of the invention can be accomplished by a variety of techniques known to those skilled in the art. These techniques include stirring techniques (manually and with magnetic stirring systems), vortexing techniques, vibration techniques, and sonication techniques. Sonication techniques are typically accomplished using a steel probe that resonates at high frequency vibrations.

In other preferred embodiments, the invention relates to the method of treating or preventing an abnormal condition in a patient in need of such treatment. The method comprises the following steps: (a) diluting a parenteral formulation into a pharmaceutically acceptable solution, said parenteral formulation comprising one or more hydrophobic pharmaceutical agents, that are independently selected from the group consisting of quinazoline-, nitrothiazole-, and indolinone-based compounds; one or more polyoxyhydrocarbyl compounds; and one or more pharmaceutically acceptable surfactants; and (b) parenterally administering the diluted formulation to the patient. In some highly preferred embodiments, the formulation further comprises one or more pharmaceutically acceptable alcohols.

Preferably, the one or more hydrophobic pharmaceutical agents are chosen from a group selected for their positive results in one or more in vitro assays that corresponds to the disease or to the disorder to be treated. Examples of such assays are described in section III of the Detailed Description of the Invention.

In preferred embodiments, the pharmaceutically acceptable solution is selected from the group consisting of saline, 0.45% N saline, WFI (water for injection), D5W (5% dextrose in water), and D5W 0.45% N saline. The ratio of the formulation volume to the pharmaceutically acceptable solution volume is preferably 10:1 to 1:2 (v/v), more preferably 2:1 to 1:3 (v/v), and most preferably 1:1, 1:2, or 1:3 (v/v).

In other preferred embodiments, the invention features a method of treating a patient in need of such treatment using a formulation that comprises: (a) 0.1 to 100 mg/mL of an indolinone-based compound of formula VI, where $R_1$, $R_2$, $R_3$, and $R_4$ are selected from the group consisting of hydrogen, trihalomethyl, hydroxyl, amine, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and $R_5$ is an optionally substituted aryl or heteroaryl cyclic moiety; (b) 0.01 to 10 g/mL PEG-400; (c) 0.01 to 1 g/mL ethanol; (d) 0.001 to 1 g/mL benzyl alcohol; and (e) 0.01 to 10 g/mL ethoxylated castor oil.

In yet other methods of treatment the formulation comprises: (a) about 5.0 mg/mL of an indolinone-based compound of formula VI, where $R_1$, $R_2$, $R_3$, and $R_4$ are selected from the group consisting of hydrogen, trihalomethyl, hydroxyl, amine, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and $R_5$ is an optionally substituted aryl or heteroaryl cyclic moiety; (b) about 0.35 g/mL PEG-400; (c)about 0.114 g/mL ethanol; (d) about 0.02 g/mL benzyl alcohol; and (e) about 0.25 g/mL CREMOPHOR EL®.

In a highly preferred embodiment of a method of treatment, the formulation comprises: (a) about 4.5 mg/mL of an indolinone-based compound, 3-[(2,4-dimethylpyrrol-5-yl)methylene]-2-indolinone; (b) about 45% w/v PEG-400; (c) about 31.5% w/v CREMOPHOR EL®; (d) about 2% w/v benzyl alcohol; and (e) about 9.5% w/v ethanol.

In another aspect, the invention relates to a method of preventing or treating an abnormal condition in a patient in need of treatment comprising the following steps: (a) preparing an acceptable pharmaceutical composition from an oral formulation, said oral formulation comprising: a hydrophobic pharmaceutical agent, one or more polyoxyhydrocarbyl compounds, one or more polyglycolized lipids, and one or more pharmaceutically acceptable surfactants; and (b) administering said composition to said patient. Preferably, the formulation is orally administered. In highly preferable embodiments, the oral formulation further comprises one or more pharmaceutically acceptable oils.

The pharmaceutically acceptable composition is preferably selected from the group comprising: said oral formulation, a hard gelatin capsule filled with said oral formulation, a soft gelatin capsule filled with said oral formulation, and a hard gelatin capsule filled with said oral composition admixed with a granulating agent to form a dry solid composition. In preferred embodiments, the solution is encapsulated in a soft elastic gelatin capsule (SEC) or a hard gelatin capsule.

A solid composition of the formulation can be prepared by mixing the formulation in a liquefied state with a pharmaceutically acceptable granulating agent or a mixture of pharmaceutically acceptable granulating agents (for example silicon dioxide, microcrystalline cellulose, starch, calcium carbonate, pectin, crospovidone, polyplasdone and the like).

In preferred embodiments of the method of treatment, the formulation comprises: (a) about 3% w/w of an indolinone-based compound of formula VI, where $R_1$, $R_2$, $R_3$, and $R_4$ are selected from the group consisting of hydrogen, trihalomethyl, hydroxyl, amine, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and $R_5$ is an optionally substituted aryl or heteroaryl cyclic moiety; (b) about 70% w/w GELUCIRE® 44/14; (c) about 10% w/w CREMOPHOR EL®; (d) about 10% w/w Miglyol 812; and (e) about 10% w/w polyethylene glycol 600.

In other preferred embodiments of the method of treatment, the formulation comprises: (a) about 3% w/w of an indolinone-based compound of formula VI, where $R_1$, $R_2$, $R_3$, and $R_4$ are selected from the group consisting of hydrogen, trihalomethyl, hydroxyl, amine, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and $R_5$ is an optionally substituted aryl or heteroaryl cyclic moiety; (b) about 76% w/w LABRA-SOL®; (c) about 12% w/w CREMOPHOR EL®; and (d) about 12% w/w polyethylene glycol 600.

In yet other preferred embodiments of the method of treatment, the formulation comprises: (a) about 3% w/w of an indolinone-based compound of formula VI, where $R_1$, $R_2$, $R_3$, and $R_4$ are selected from the group consisting of hydrogen, trihalomethyl, hydroxyl, amine, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and $R_5$ is an optionally substituted aryl or heteroaryl cyclic moiety; (b) about 70% w/w LABRA-SOL®; (c) about 109 w/w CREMOPHOR EL®; (d) about 10% w/w Miglyol 812; and (e) about 10% w/w polyethylene glycol 600.

In preferred embodiments of the method of treatment, the parenteral or oral formulations comprise an indolinone-based compound having a structure of formula VI, where $R_1$, $R_2$, $R_3$, and $R_4$ are selected from the group consisting of hydrogen, trihalomethyl, hydroxyl, amine, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and $R_5$ is an optionally substituted aryl or heteroaryl cyclic moiety.

In other preferred embodiments of the method of treatment, the parenteral or oral formulations comprise an indolinone-based compound having a structure of formula VI, where $R_1$, $R_2$, $R_3$, and $R_4$ are selected from the group consisting of hydrogen, halogen, alkyl, and alkoxy; and where $R_5$ is a pyrrolyl or thiophenyl moiety optionally substituted with moieties selected from the group consisting of hydrogen, halogen, alkyl, and alkoxy.

In other preferred embodiments of the method of treatment, the parenteral or oral formulations comprise an indolinone-based compound selected from the group consisting of 3-[(2,4-dimethylpyrrol-5-yl)methylene]-(5-amino)-2-indolinone, 3-[(2,4-dimethylpyrrol-5-yl)methylene]-(5-chloro)-2-indolinone, 3-[(2,4 -dimethylpyrrol-5-yl)methylene]-2-indolinone, and 3-[(3-methylthiophenyl-5-yl)methylene]-(4-methyl)-2-indolinone.

In highly preferred embodiments of the method of treatment, the parenteral or oral formulations comprise the indolinone-based compound, 3-[(2,4-dimethylpyrrol-5-yl)methylene]-2-indolinone.

In highly preferred embodiments of the invention, the method of treatment is effective in treating or preventing an abnormal condition in a patient, preferably a mammal, more preferably a human, in need of such treatment. Abnormal conditions which may be treated with these formulations are cell proliferative disorders, typically those characterized by abnormal protein kinase activity. Preferably, the formulation inhibits protein kinase activity.

Other features and advantages of the invention will be apparent from the following description of the preferred embodiments and from the claims.

DESCRIPTION OF FIGURES

FIGS. 1A and B shows a summary of exemplary formulations tested for oral bioavailability.

FIGS. 2A and B shows a summary of exemplary dosing regimens for the oral bioavailability studies.

DETAILED DESCRIPTION OF THE INVENTION

The present invention features parenteral and oral formulations for solubilizing hydrophobic pharmaceutical agents, including quinazoline-, nitrothiazole- and indolinone-based compounds. The formulations can be used to facilitate administration of hydrophobic pharmaceutical compounds to patients in need of such treatment.

The invention is directed in part towards administering hydrophobic pharmaceutical agents in parenteral and oral formulations that obliterate tumors by severing their sources of sustenance. The hydrophobic pharmaceutical agents are designed to specifically bind protein kinases over-expressed in the vasculature that supply tumors with sustenance. One such protein kinase target (particularly of indolinone-based compounds) is FLK-1, which is over-expressed in the proliferating endothelial cells of a growing tumor, but not in the surrounding quiescent endothelial cells (Plate et al., 1992, *Nature* 359:845–848).

FLK-1 is activated upon binding VEGF, a strong regulator for endothelial cell proliferation as well as normal and pathological angiogenesis (Klagsburn and Soker, 1993, *Current Biology* 3:699–702). Thus, compounds that specifically inhibit the FLK protein kinase are potential anti-cancer agents as they may decrease the vasculature that nourishes tumors. These inhibitors will most likely result in minimizing and even obliterating solid tumors. In addition, compounds that specifically inhibit FLK will potentially represent a new generation of cancer therapeutics as they will most likely cause few side effects. These potential properties are a welcome improvement over the currently utilized cancer therapeutics that cause multiple side effects and deleteriously weaken patients.

Another kinase target of the hydrophobic pharmaceutical agents of the invention (particularly quinazoline-based compounds) is RAF, a serine/threonine protein kinase. RAF is a non-receptor protein kinase that is recruited to the cell membrane when it binds to activated RAS, a guanine triphosphate hydrolyzing enzyme. RAS is activated when an activated receptor protein tyrosine kinase, such as EGFR or PDGFR, bind to an adaptor protein, GRB2, and a guanine nucleotide exchange factor, SOS. SOS removes guanine diphosphate from RAS, replaces it with guanine triphosphate, and thereby activates RAS. RAS then binds RAF and consequently activates RAF. RAF may then phosphorylate other protein targets on serine and threonine residues, such as the kinase (MEK) that phosphorylates and consequently activates mitogen-activated protein kinase (MAPK). Thus, RAF serves as an intermediary controlling factor in mitogen-activated signal transduction.

Due to the important regulatory role of RAF in cells, modifications to the amino acid sequence of RAF can alter its function and consequently modify cellular behavior. RAF's role in cell proliferation is underscored by the observation that mutations to RAF's amino acid sequence have been associated with tumors and cancers. Because the mutations to RAF that give rise to cancer in cells lead to RAF molecules that display unregulated catalytic activity, inhibitors of RAF may alleviate or even abrogate the cell proliferation that leads to cancer in these cells.

Some quinazoline-based compounds are known to inhibit the function of the RAF protein kinase (U.S. application Ser. No. 60/045,351, by Tang et al., filed May 2, 1997). Because RAF exhibits significant amino acid homology to other serine/threonine protein kinases, quinazoline-based compounds may inhibit serine/threonine protein kinases other than RAF.

Yet another target of the hydrophobic pharmaceutical agents of the present invention (and in particular nitrothiazole-based compounds) are protein tyrosine phosphatases (PTPs). Protein tyrosine phosphatases comprise a family of transmembrane and cytoplasmic enzymes that are involved in cell signaling cascades. The substrates of PTPs may be protein tyrosine kinases (PTKs) which possess phosphotyrosine residues or the substrates of PTKs (Hunter, 1989, Cell 58:1013–16; Fischer et al., 1991, Science 253:401–6; Saito & Streuli, 1991, Cell Growth and Differentiation 2:59–65; Pot and Dixon, 1992, Biochem. Biophys. Acta, 1136:35–43). A common mechanism by which receptors regulate cell function is through an inducible tyrosine kinase activity which is either endogenous to the receptor or is imparted by other proteins that become associated with the receptor (Darnell et al., 1994, Science 264:1415–1421; Heldin, 1995, Cell 80:213–223; Pawson, 1995, Nature 373:573–580).

Protein tyrosine kinases comprise a large family of transmembrane receptor and intracellular enzymes with multiple functional domains (Taylor et al., 1992 Ann. Rev. Cell Biol. 8:429–62). Included among the PTKs are epidermal growth factor receptor (EGFR) and platelet-derived growth factor receptor (PDGFR), which undergo oligomerization upon ligand binding, and the receptors self-phosphorylate (via autophosphorylation or transphosphorylation) on specific tyrosine residues in the cytoplasmic portions of the receptor (Schlessinger and Ullrich, 1992, Neuron, 9:383–91, Heldin, 1995, Cell 80:213–223). Other members include cytoplasmic protein tyrosine kinases (CPTKs), such as Janus kinases (e.g., JAK1, JAK2, TYK2), Src kinases (e.g., src, lck, fyn) that are associated with receptors for cytokines (e.g., IL-2, IL-3, IL-6, erythropoietin) and interferons, and antigen receptors. These receptors also undergo oligomerization, and have tyrosine residues that become phosphorylated during activation, but the receptor polypeptides themselves do not possess kinase activity.

The levels of tyrosine phosphorylation required for normal cell growth and differentiation at any time are achieved through the coordinated action of PTKs and PTPs. Depending on the cellular context, these two types of enzymes may either antagonize or cooperate with each other during signal transduction. An imbalance between these enzymes may impair normal cell functions leading to metabolic disorders and cellular transformation.

I. Target Diseases to be Treated by Hydrophobic Pharmaceutical Agent Formulations The hydrophobic pharmaceutical agents of the invention can be used as kinase inhibitors, antimetastatic or anticancer agents, or to control angiogenesis; for inhibiting atheromatous plaque development; for treating Alzheimer's disease; and as immunomodulators. The current invention can be used in the treatment of psoriasis, epidermal hyperproliferation, restenosis, diabetic complications, and as immunosuppressants.

Protein kinases are essential regulatory molecules that control a variety of cellular functions. For this reason, any alteration in the function of a protein kinase can cause an abnormal condition in an organism. One of the many functions controlled by protein kinases is cell proliferation.

Alterations in the function of a protein kinase that normally regulates cell proliferation can lead to enhanced or decreased cell proliferative conditions evident in certain diseases. Aberrant cell proliferative conditions include cancers such as fibrotic and mesangial disorders, abnormal angiogenesis and vasculogenesis, wound healing, psoriasis, restenosis, diabetes mellitus, and inflammation.

Fibrotic disorders relate to the abnormal formation of the cellular extracellular matrix. An example of a fibrotic disorder is hepatic cirrhosis. Hepatic cirrhosis is characterized by an increased concentration of extracellular matrix constituents resulting in the formation of a hepatic scar. Hepatic cirrhosis can cause diseases such as cirrhosis of the liver.

Mesangial cell proliferative disorders occur due to the abnormal proliferation of mesangial cells. Mesangial proliferative disorders include various human renal diseases, such as glomerulonephritis, diabetic nephropathy, malignant nephrosclerosis, thrombotic microangiopathy syndromes, transplant rejection, and glomerulopathies.

Angiogenic and vasculogenic disorders result from excess proliferation of blood vessels. Blood vessel proliferation is necessary in a variety of normal physiological processes such as embryonic development, corpus luteum formation, wound healing and organ regeneration. However, blood vessel proliferation is also essential in cancer tumor development. Other examples of blood vessel proliferative disorders include arthritis, where new capillary blood vessels invade the joint and destroy cartilage. In addition, blood vessel proliferative diseases include ocular diseases, such as diabetic retinopathy, where new capillaries in the retina invade the vitreous, bleed and cause blindness. Conversely, disorders related to the shrinkage, contraction or closing of blood vessels, such as restenosis, are also implicated in adverse regulation of protein kinases and protein phosphatases.

Moreover, vasculogenesis and angiogenesis are associated with the growth of malignant solid tumors and metastasis. A vigorously growing cancer tumor requires a nutrient and oxygen rich blood supply to continue growing. As a consequence, an abnormally large number of capillary blood vessels often grow in concert with the tumor and act as supply lines to the tumor. In addition to supplying nutrients to the tumor, the new blood vessels embedded in a tumor provide a gateway for tumor cells to enter the circulation and metastasize to distant sites in the organism (Folkman, 1990, J. Natl. Cancer Inst. 82:4–6).

II. Synthesis of Hydrophobic Pharmaceutical Agents

The indolinone-based compounds of the invention are synthesized by reacting an aldehyde with an indolinone. Descriptions of methods for synthesizing indolinone-based compounds are provided in U.S. application Ser. No. 08/702,282 and PCT Publication No. WO 96/40116, published Dec. 19, 1996, both of which are incorporated herein by reference in their entirety, including any drawings and figures. The examples fully describe the solvents, temperatures, separation techniques, and other conditions utilized for the invention. Other synthetic techniques, such as those described in International patent publication WO 96/22976, published Aug. 1, 1996 may also be used or modified by those skilled in the art to make the compounds of the resent invention.

The quinazoline-based compounds of the invention are synthesized following the description of the methods provided in U.S. application Ser. No. 60/045,351, by Tang et al., filed May 2, 1997, incorporated herein by reference in its entirety, including any drawings or figures. The examples fully describe the solvents, temperatures, separation techniques, and other conditions utilized for the invention.

The quinazoline compounds of the invention are synthesized using the following general procedure unless otherwise stated:

(i) evaporation were carried out by rotary evaporation in vacuo;

(ii) operations were carried out under an atmosphere of an inert gas such as nitrogen;

(iii) high performance liquid chromatography (HPLC) were performed on Merck LiChrosorb RP-18 reversed-phase silica obtained from E. Merck, Darmstadt, Germany;

(iv) yields are given for illustration only and are not necessarily the maximum attainable;

(v) melting points are uncorrected and were determined using a HWS Mainz SG 2000 digital melting point apparatus;

(vi) the structures of all compounds of the formula (I), (II), and (III) of this invention were confirmed by proton magnetic resonance spectroscopy on a Bruker AMX500-NMR spectrophotometer, by elemental microanalysis and, in certain cases, by mass spectroscopy;

(vii) the purity of the structures were performed by thin layer chromatography (TLC) using silica gel (Merck Silica Gel 60 F254) or by HPLC;

(viii) intermediates were not generally fully characterised and purity was assessed by thin layer chromatography (TLC) or by HPLC.

It should be understood that the invention is not limited to the particular embodiments shown and described herein, but that various changes and modifications may be made without departing from the spirit and scope of the invention as defined by the claims. The following specific procedures were utilized to synthesize quinazoline compounds of the invention.

Procedure A

Method for Reaction of 2,4-Diamino-5-Fluoroquinazoline with Sodium Phenolates and Thiophenolates:

Dimethyl sulphoxide and sodium hydride (80% disp in mineral oil) was added to a dry flask maintained under inert atmosphere at room temperature. A solution of phenol (optionally substituted) in dimethyl sulphoxide was added to the stirred reaction mixture, heated to 60° C. for 30 minutes and allowed to cool. 2,4-Diamino-5-fluoroquinazoline was added all at once (as the solid) and the reaction mixture was heated to ca 150° C. for 2–3 hours. After cooling to room temperature the suspension was diluted with water and e.g. with methanol, the solid collected by filtration, washed, recrystallized and dried at 50° C. in vacuo. 2,4-Diamino-5-fluoroquinazoline was prepared from 2,6-difluorobenzonitrile (Lancaster, Acros) according to the published method (*J. Heterocyclic. Chem.* 25, 1173 (1988)).

The following compounds have been obtained according to this procedure:

1. 2,4-Diamino-5-(4-methoxyphenoxy)quinazoline, m.p. 268–270° C.

2. 2,4-Diamino-5-(3-trifluormethylphenoxy)quinazoline, m.p. 280–284° C. (dec)

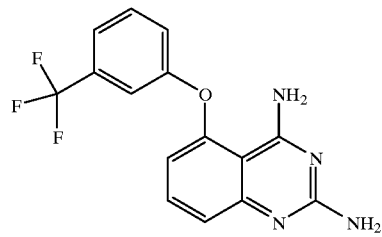

2,4-Diamino-5-phenylthioquinazoline was also synthesized by the following method: 2,4-Diamino-5-fluoroquinazoline (3.6 g, 20 mmol) and sodium thiophenolate (Fluka) (3.2 g, 24 mmol) in DMSO (100 ml) were reacted at 75° C. for 15 hours. After cooling to room temperature the suspension was diluted with water (25 ml) and methanol (150 ml), the solid was collected by filtration, washed with methanol, recrystallized from n-butyl acetate and dried at 50° C. in vacuo to give 2,4-diamino-5-phenylthioquinazoline (1.0 g, 18.60%, m.p. 240–244° C.):

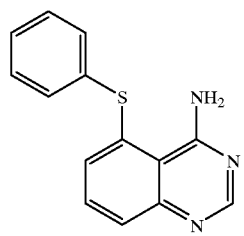

Procedure B

Method for Reaction of 2,4-Diamino-5-Fluoroquinazoline with Potassium Phenolates:

To a stirred solution of potassium tert-butoxide in dimethyl sulphoxide under nitrogen phenol (optionally substituted) and after evolution of hydrogen had ceased 2,4-diamino-5-fluoroquinazoline were added all at once (as the solid) and the mixture was heated to ca 150° C. for 2–3 hours. After cooling to room temperature the suspension was diluted with water and e.g. with methanol, the solid was collected by filtration, washed, and dried at 50° C. in vacuo. The following compounds have been obtained according to this procedure:

1. 2,4-Diamino-5-(4-tert-butylphenoxy)quinazoline, m.p. 226–228° C.

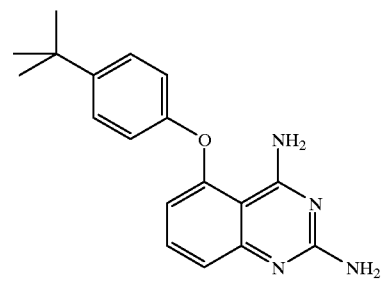

2. 2,4-Diamino-5-(3,4-dimethoxyphenoxy)quinazoline, m.p. 301–302° C.

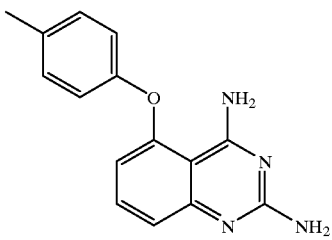

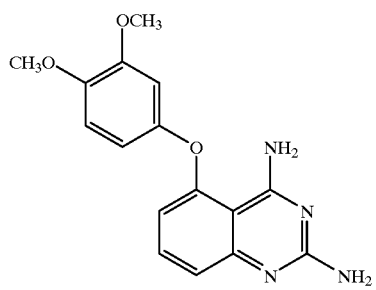

3. 2,4-Diamino-5-(3-dimethylaminophenoxy)quinazoline, m.p. 224–225° C. (dec)

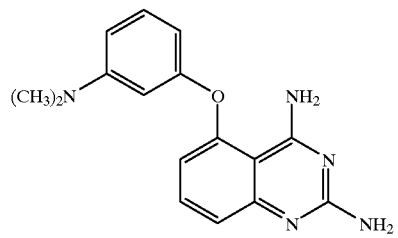

4. 2,4-Diamino-5-(2-fluorophenoxv)quinazoline, m.p. 301 303° C.
5. 2,4-Diamino-5-(3-bromophenoxy)quinazoline, m.p. 292–295° C.
6. 2,4-Diamino-5-(2-methoxyphenoxy)quinazoline, m.p. 208–209° C. (dec)
7. 2.4-Diamino-5-(3-methoxyphenoxy)quinazoline, m.p. 215–216° C. (dec)
8. 2,4-Diamino-5-(4-benzyloxyphenoxy)quinazoline, m.p. 175–177° C.
9. 2,4-Diamino-5-(3-dimethylaminopropoxy)quinazoline, m.p. 193–195° C.

In addition, the following compounds may be synthesized by either method A or method C, described below:

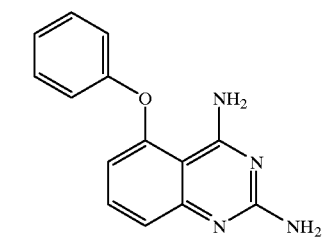

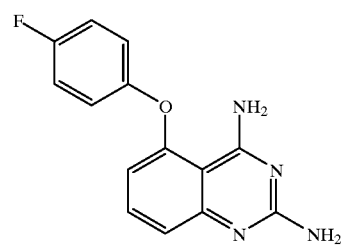

-continued

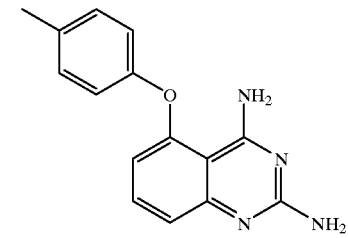

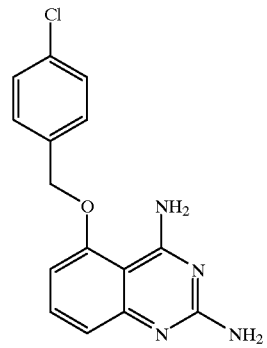

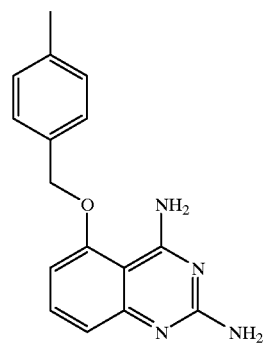

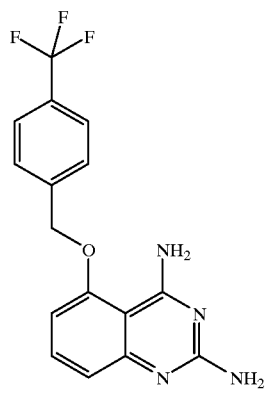

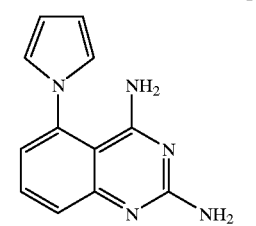

Procedure C

Method for Reaction of 4-Amino-5-Fluoroquinazoline with Potassium Phenolates and Sodium Thiophenolate:

A solution of phenol (optionally substituted) in dimethyl suiphoxide was added to a stirred mixture of potassium tert-butoxide in dimethyl suiphoxide at room temperature.

After 15 minutes 2,4-diamino-5-fluoroquinazoline was added all at once (as the solid) and the mixture was heated to ca 50° C. for 7 hours. After cooling to room temperature the suspension was diluted with water, the solid collected by is filtration, washed, recrystallized from ethanol or n-butyl acetate and dried at 50° C. in vacuo. In particular, 4-Amino-5-fluoroquinazoline was prepared from 2,6-difluorobenzonitrile (Lancaster, Acros) according to the published method (*J. Heterocyclic. Chem.* 28, 1357 (1991)).

The following compounds have been obtained according to this procedure:

1. 4-Amino-5-(4-methoxyphenoxy)quinazoline, m.p. 192–195° C.

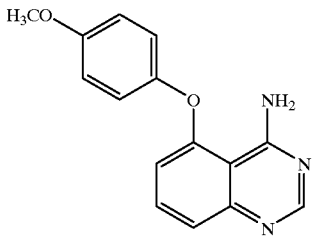

2. 4-Amino-5-(3-dimethylaminophenoxy)quinazoline, m.p. 179–181° C.
3. 4-Amino-5-(3-pyridinoxy)quinazoline, m.p. 245–247° C.
4. 4-Amino-5-(4-benzyloxyphenoxy)quinazoline, m.p. 170–171° C.
5. 4-Amino-5-(3,4-methylenedioxyphenoxy)quinazoline, m.p. 201–203° C.

Procedure D

Method for Reaction of 6-Substituted 2-Fluorobenzonitriles with Guanidine Carbonate:

A mixture of 1 equivalent of 6-substituted 2-fluorobenzonitriles (Maybridge, Lancaster) and 1.5 equivalent of guanidine carbonate in N,N-dimethylacetamide was heated under nitrogen at 140–150° C. for 5–6 hours. The reaction mixture was allowed to cool to room temperature overnight. The resulting suspension was diluted with water and e.g. with methanol, and after cooling to 4° C. the solid was collected by filtration, washed, recrystallized from n-butyl acetate, filtrated again and dried at 50° C. in vacuo.

The following compounds have been obtained according to this procedure:

1. 2,4-Diamino-5-(4-chlorophenylthio)quinazoline, m.p. 220–224° C.

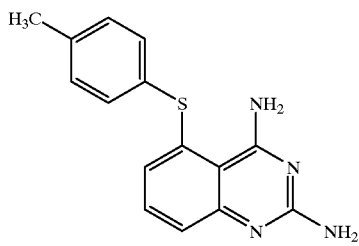

2. 2,4-Diamino-5-(4-methylphenylthio)quinazoline, m.p. 206–207° C.

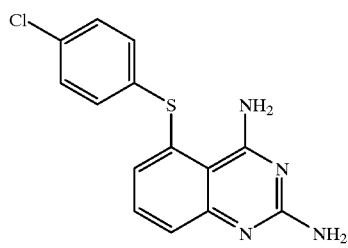

3. 2,4-Diamino-5-methoxyquinazoline, m.p. 199–202° C.
4. 2,4-Diamino-5-(pyrrol-1-yl)quinazoline, m.p. 248–250° C.

In similar synthetic processes, the following compounds can be synthesized:

1. 4-Amino-5-(4-fluorophenoxy)quinazoline was prepared from 2-fluoro-6-(4-fluorophenoxy) benzonitrile (Maybridge) as follows:

A mixture of 2-fluoro-6-(4-fluorophenoxy)benzonitrile (2.5 g, 11 mmol) and formamidine acetate (Aldrich) (2.3 g, 22 mmol) in 50 ml of N,N-dimethylacetamide was heated at 162° C. under nitrogen for 9 hours. After cooling to room temperature the reaction mixture was evaporated under reduced pressure. The product was suspended in 80 ml of cold water and the pH adjusted to 8.5 with concentrated ammonium hydroxide. After cooling the suspension overnight, the precipitate was isolated by filtration, washed with water (25 ml), dried and recrystallized from 30 ml of ethanol at 4° C. The precipitate was collected by filtration, washed with ethanol and dried at 50° C. in vacuo to give 4-amino-5-(4-fluorophenoxy)quinazoline (0.3 g, 10.7%, m.p. 188–190° C.):

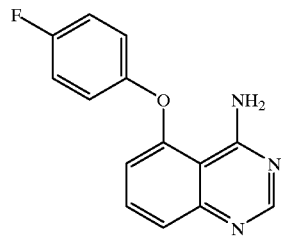

2. 4-Amino-2-phenyl-5-phenoxyquinazoline was prepared from 2-fluoro-6-phenoxybenzonitrile (Maybridge) as follows:

A mixture of 2-fluoro-6-phenoxybenzonitrile (2.7 g, 13 mmol), benzamidine hydrochloride (Aldrich) (3.0 g, 19 mmol) and sodium acetate (1.6 g, 19 mmol) in 60 ml of N,N-dimethylacetamide was heated at 150° C. under nitrogen for 6.5 hours. After cooling to room temperature the reaction mixture was evaporated under reduced pressure. The product was suspended in 20 ml of ethanol and water (100 ml) and concentrated ammonium hydroxide (10 ml) was added. The precipitate was isolated by filtration, washed with water, dried and recrystallized twice from 60 ml of 2-propanol at 4° C. The precipitate was collected by filtration, washed with 2-propanol and dried at 50° C. in vacuo to give 4-amino-2-phenyl-5-phenoxyquinazoline (0.5 g, 12%, m.p. 190–191° C.):

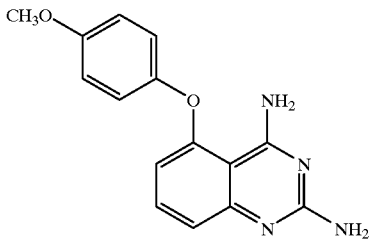

The following procedures can be utilized to synthesize compounds related to those described herein:

Procedure E

Method for Reaction of 5-Substituted 4-Aminoquinazolines with Aryl Isocyanates:

To a stirred solution of the 5-substituted 4-aminoquinazoline in dichloromethane aryl isocyanate (optionally substituted) was added at room temperature and stirring continued overnight. The precipitate was collected, washed with dichloromethane and dried at 50° C. in vacuo.

1-[5-(4-Methoxyphenoxy)Quinazolin-4-Yl]-3-Phenylurea:

4-Amino-5-(4-methoxyphenoxy)Quinazoline (1.0 g, 3.7 mmol) and phenyl isocyanate (0.52 g, 4.4 mmol) were reacted in 30 ml of dichloromethane according to procedure E to give 1-[5-(4-methoxyphenoxy)quinazolin-4-yl]-3-phenylurea (0.9 g, 64.3%, m.p. 231–232° C.).

1-[5-(4-Methoxyphenoxy)Quinazolin-4-Yl]-3-(3-Bromophenyl)Urea:

4-Amino-5-(4-methoxyphenoxy)quinazoline (0.35 g, 1.3 mmol) and 3-bromophenyl isocyanate (0.31 g, 1.6 mmol) were reacted in 20 ml of dichloromethane according to procedure E to give 1-[5-(4-methoxyphenoxy)quinazolin-4-yl]-3-(3-bromophenyl)urea (0.5 g, 83.3%, m.p. 249–251° C.)

1-[5-(4-Methoxyphenoxy)Quinazolin-4-Yl]-3-(3-Methoxyphenyl)Urea:

4-Amino-5-(4-methoxyphenoxy)quinazoline (0.35 g, 1.3 mmol) and 3-methoxyphenyl isocyanate (0.23 g, 1.6 mmol) were reacted in 20 ml of dichloromethane according to procedure E to give 1-[5-(4-methoxyphenoxy)quinazolin-4-yl]-3-(3-methoxyphenyl)urea (0.4 g, 74.1%, m. p. 209–210° C.).

4-Amino-5-Phenylthioquinazoline

4-Amino-5-fluoroquinazoline (3.2 g, 20 mmol) and sodium thiophenolate (Fluka) (4.0 g, 30 mmol) in DMSO (80 ml) were reacted at 150° C. for 5 hours. After cooling to room temperature the suspension was diluted with water (100 ml) and ethanol (50 ml), the solid was collected by filtration, washed (water/ethanol 1:1), recrystallized from 2-propanol and dried at 50° C. in vacuo to give 2,4-diamino-5-phenylthioquinazoline (2.1 g, 41.4%, m.p. 195–197° C.).

2,4-Diamino-5-Anilinoquinazoline

Aniline (Aldrich) (5 g, 50 mmol), sodium hydride (80% disp in mineral oil) (1.5 g, 50 mmol) and 2,4-diamino-5-fluoroquinazoline (4.4 g, 25 mmol) were reacted in 80 ml of dimethyl sulphoxide according to procedure A to give 2,4-diamino-5-anilinoquinazoline (0.3 g, 4.8%, m.p. 279–283° C. (dec)).

4-Acetamido-5-(4-Methoxyphenoxy)Quinazoline was Prepared from 4-amino-5-(4Methoxyphenoxy)Quinazoline as follows:

To a stirred solution of 4-amino-5-(4-methoxyphenoxy) quinazoline (1.0 g, 3.7 mmol) in 30 ml of dichloromethane pyridine (0.3 g, 3.7 mmol) and acetic anhydride (0.38 g, 3.7 mmol) were added at room temperature and stirring continued for 4 days. After evaporation under reduced pressure, 30 ml of 2-propanol was added and after cooling to 4° C. the solid was collected by filtration, washed, recrystallized from ethanol, filtrated again and dried at 50° C. in vacuo. to give 4-acetamido-5-(4methoxyphenoxy)quinazoline (0.5 g, 45.4%, m.p. 174–175° C.).

4-Amino-5-(4-Hydroxyphenoxy)Quinazoline

4-Amino-5-(4-benzyloxyphenoxy)quinazoline (1.5 g, 4.4 mmol) was hydrogenated under 5 atm of $H_2$ in the presence of 0.5 g of 10% Pd/C in 80 ml of N,N-dimethylacetamide at 50–60° C. After 4 hours the reaction mixture was filtered through a glass filter of silica gel, concentrated, dissolved in 80 ml of ethanol/water 4:1 (v/v) and crystallized at 4° C. The precipitate was collected by filtration, washed with ethanol and dried at 50° C. in vacuo to give 4-amino-5-(4-hydroxyphenoxy)quinazoline (0.3 g, 27.3%, m.p. 300–302° C. (dec)).

2,4-Diamino-5-(4-Hydroxyphenoxy)Quinazoline 2,4-Diamino-5-(4-benzyloxyphenoxy)quinazoline (3.6 g, 10 mmol) was hydrogenated under 4 atm of $H_2$ in the presence of 0.36 g of 10% Pd/C in 80 ml of N,N-dimethylacetamide at 50–60° C. After 4 hours the reaction mixture was filtered through a glass filter of silica gel, concentrated, dissolved in 50 ml of 2-propanol and crystallized at 4° C. The precipitate was collected by filtration, washed with 2-propanol and dried at 50° C. in vacuo to give 2,4-diamino-5-(4-hydroxyphenoxy)quinazoline (2.3 g, 85.2%, m.p. 330–341° C. (dec)).

The nitrothiazole-based compounds of the invention are synthesized with readily available materials using standard organic synthetic chemistry techniques in accordance with the teachings of U.S. Pat. Nos. 5,198,333, 3,970,725, and 3,850,939 which are hereby incorporated by reference herein, including any drawings or figures.

III. Biological Activity of Hydrophobic Pharmaceutical Agents

Indolinone-based compounds of the invention have been tested for their ability to activate or inhibit protein kinases in biological assays. The methods used to measure indolinone-based compound modulation of protein kinase function are described in U.S. application Ser. No. 08/702,282, filed Aug. 23, 1996, incorporated herein by reference in its entirety, including any drawings. In particular, indolinone-based compounds of the invention were tested for their ability to inhibit the FLK protein kinase. The preferred indolinone-based compound of the invention, 3-[(2,4-dimethylpyrrol-5-yl)methylene]-2-indolinone, is a specific and potent inhibitor of VEGF-induced endothelial cell growth.

Quinazoline-based compounds of the present invention have been tested for their ability to inhibit RAF protein kinase function. The biological assays and results of these inhibition studies are described in U.S. application Ser. No. 60/045,351, by Tang et al., filed May 2, 1997. The methods used to measure quinazoline-based compound modulation of protein kinase function are similar to those described in U.S. application Ser. No. 08/702,282, filed Aug. 23, 1996, with respect to the high throughput aspect of the method. The Ser. No. 08/702,282 application is incorporated herein by reference in its entirety, including any drawings.

Nitrothiazole-based compounds of the present invention have been tested for their ability to inhibit protein tyrosine phosphatases by various procedures known in the art. Biological and biochemical assays and results of these inhibition studies are described in U.S. application Ser. No. 08/660,900, by Tang et al., filed Jun. 7, 1996, which is hereby incorporated herein in its entirety, including any drawings or figures. In general, such assays involve exposing target cells in culture to the compounds and a) biochemically analyzing cell lysates to assess the level and/or identity of tyrosine phosphorylated proteins; or (b) scoring phenotypic or functional changes in treated cells as compared to control cells that were not exposed to the test substance.

IV. Administration of Hydrophobic Pharmaceutical Agent Formulations

Methods of determining the dosages of compounds to be administered to a patient and modes of administering compounds to an organism are disclosed in U.S. application Ser. No. 08/702,282, filed Aug. 23, 1996 and International patent publication number WO 96/22976, published August 1 1996, both of which are incorporated herein by reference in its entirety, including any drawings. Those skilled in the art will appreciate that such descriptions are applicable to the present invention and can be easily adapted to it.

The proper dosage depends on various factors such as the type of disease being treated, the particular composition being used, and the size and physiological condition of the patient. Therapeutically effective doses for the compounds described herein can be estimated initially from cell culture and animal models. For example, a dose can be formulated in animal models to achieve a circulating concentration range that initially takes into account the $IC_{50}$ as determined in cell culture assays. The animal model data can be used to more accurately determine useful doses in humans.

Plasma half-life and biodistribution of the drug and metabolites in the plasma, tumors, and major organs can be also be determined to facilitate the selection of drugs most appropriate to inhibit a disorder. Such measurements can be carried out. For example, HPLC analysis can be performed on the plasma of animals treated with the drug and the location of radiolabeled compounds can be determined using detection methods such as X-ray, CAT scan, and MRI. Compounds that show potent inhibitory activity in the screening assays, but have poor pharmacokinetic characteristics, can be optimized by altering the chemical structure and retesting. In this regard, compounds displaying good pharmacokinetic characteristics can be used as a model.

Toxicity studies can also be carried out by measuring the blood cell composition. For example, toxicity studies can be carried out in a suitable animal test (e.g., mice in the example below) as follows: 1) the compound is administered to mice (an untreated control mouse should also be used); 2) blood samples are periodically obtained via the tail vein from one mouse in each treatment group; and 3) the samples are analyzed for red and white blood cell counts, blood cell composition, and the percent of lymphocytes versus polymorphonuclear cells. A comparison of results for each dosing regime with the controls indicates if toxicity is present.

At the termination of each toxicity study, further studies can be carried out by sacrificing the animals (preferably, in accordance with the American Veterinary Medical Association guidelines Report of the American Veterinary Medical Assoc. Panel on Euthanasia, *Journal of American Veterinary Medical Assoc.*, 202:229–249, 1993). Representative animals from each treatment group can then be examined by gross necropsy for immediate evidence of metastasis, unusual illness, or toxicity. Gross abnormalities in tissue are noted, and tissues are examined histologically. Compounds causing a reduction in body weight or blood components are less preferred, as are compounds having an adverse effect on major organs. In general, the greater the adverse effect the less preferred the compound.

For the treatment of cancers the expected daily dose of a hydrophobic pharmaceutical agent is between 1 to 500 mg/day, preferably 1 to 250 mg/day, and most preferably 1 to 50 mg/day. Drugs can be delivered less frequently provided plasma levels of the active moiety are sufficient to maintain therapeutic effectiveness.

Plasma levels should reflect the potency of the drug. Generally, the more potent the compound the lower the plasma levels necessary to achieve efficacy.

V. Hydrophobic Pharmaceutical Agent Formulations

The formulations of the invention solubilize hydrophobic pharmaceutical agents, such as quinazoline-, nitrothiazole-, and indolinone-based compounds. Because these pharmaceutical agents are typically insoluble in aqueous environments, they require the addition of compounds that can solubilize them before administration of the pharmaceutical agents to a patient.

For example, the preferred indolinone-based compound of the invention, 3-[(2,4-dimethylpyrrol-5-yl)methylene]-2-indolinone, has low solubility in water (10 ng/mL), water miscible non-aqueous solvents, and oils. An increase in the indolinone-based compound's aqueous solubility in hydrotropic solute solutions like nicotinamide and pyridoxine hydrochloride was observed. It is soluble (15–20 mg/mL) in polar excipients like polyethylene glycols of 300 and 400 MW. Among the several excipients studied, the indolinone-based compound had comparatively higher solubility (10–15 mg/mL) in aromatic solvents like benzyl alcohol and in polyglycolized lipids (25–30 mg/mL) like LABRASOL and GELUCIRE.

The indolinone-based compound is a planar aromatic compound and is non-ionizable in the pharmaceutically acceptable range. The pH of the aqueous media, therefore, did not influence its aqueous solubility and it could not be converted to any salt form. It is lipophilic, with a theoretical logP (octanol-water partition co-efficient) of 3.76 and a log of ratio of octanol to water solubility (individually determined) of 5.6.

While not being limited by any particular mechanism of action, it is believed that the components of the formulations described herein bind to the hydrophobic regions of the pharmaceutical agents. This consequently exposes the polar regions of the solubilizing components to the solvent environment. This encapsulation of the pharmaceutical agents renders them soluble in aqueous environments.

The components of the formulations solubilize pharmaceutical agents in specific concentrations depending on the concentration of the pharmaceutical agents in a formulation. Thus, the pharmaceutical agents may precipitate out of solution when the concentrations of the formulation components are outside the prescribed ranges set forth herein.

For both parenteral and oral formulations, the pharmaceutical agents will likely precipitate out of solution when the concentration of polyoxyhydrocarbyl compound is not between 0.01 to 10 g/mL, and the surfactant concentration is not between 0.01 to 10 g/mL. In some formulations, the pharmaceutical agents will likely precipitate out of solution when the ethanol concentration is not between 0.01 to 1 g/mL and/or when the benzyl alcohol concentration is not between 0.001 to 1 g/mL. In oral formulations, the hydrophobic pharmaceutical agent will likely precipitate out of solution when the polyglycolized lipid concentration is not between 0.01 to 10 g/mL. In some oral formulations, the hydrophobic pharmaceutical agent will likely precipitate out of solution when the concentration of pharmaceutically acceptable oils is not between 0.01 to 10 g/mL.

EXAMPLES

The examples below are not limiting and are merely representative of various aspects and features of the present invention. The examples demonstrate methods of testing the solubility of the hydrophobic pharmaceutical agents in the formulations. In addition, the examples illustrate preparation procedures for the formulations of the invention.

Example 1

Parenteral Formulations of Indolinone-based Compounds

The feasibility of developing different types of parenteral formulations including cosolvent-surfactant based formulations, emulsion formulations and liposome based formulations was studied. Based on the ease of development and drug strength, a cosolvent based formulation was chosen.

Formulations were prepared for 3-[(2,4-dimethylpyrrol-5-yl)methylene]-2-indolinone. The compositions for three parenteral formulations that enhance the solubility of the indolinone-based compound are given in Table 3.

TABLE 3

Composition of Parenteral Formulations: 772-22, 772-69, 772-64

| | Injection Concentrate, Concentration % w/v | | |
|---|---|---|---|
| Excipients | 772-22 | 772-69 | 772-64 |
| indolinone (mg/mL) | 5.0 | 6.0 | 5 |
| PEG-400 | 35 | 45 | 30 |
| Cremophor EL | 25 | 30 | 40 |
| Benzyl Alcohol | 2 | 2 | 2 |
| Ethanol (anhydrous) | 11.4 | 23 | 30 |
| Sterile Water | add to 100 mL | add to 100 mL | add to 100 mL |

*all concentrations are in % w/v

Formulations 772-22, 772-69, and 772-64 were diluted with water in a 1:1 ratio. In addition, the 772-22, 772-69, and 772-64 formulations were diluted in 0.45 WO saline, at 1:1, 1:2, and 1:3 ratios respectively, before final intravenous administration.

The 772-22, 772-69, and 772-64 formulations can be used for other water insoluble drugs, including other indolinone-based compounds and other hydrophobic pharmaceutical agents of the invention, such as quinazoline- and nitrothiazole-based compounds. A drug even more hydrophobic than those disclosed herein would likely be solubilized by the formulation of the invention. The solubilization of a drug more hydrophobic than those disclosed herein could also be optimized by slightly modifying the amount of surfactant and/or polyethylene glycol concentrations.

In addition, the drug concentration can be increased or decreased without modifying the contents of the formulations described herein. The formulation composition can be slightly modified to accommodate substantial increases or decreases in drug concentration by, for example, increasing or decreasing the concentration of surfactant and/or polyethylene glycol. The concentrations of alcohols can also be modified in the formulation to accommodate different drug concentrations.

The preferred parenteral formulation is given in Table 4.

TABLE 4

Composition of IV formulation

| Excipients | Concentration % w/v |
|---|---|
| Indolinone | 4.5 mg/mL |
| PEG-400 | 45 |
| CREMOPHOR EL ® | 31.5 |
| Benzyl alcohol | 2 |
| Ethanol | qs |

Example 2

Parenteral Formulation Procedures

The protocol for the generic method used to prepare parenteral formulations of the invention is given below.

Generic Parenteral Formulation Preparation:

1. Weigh appropriate amounts of PEG-400.
2. Dissolve drug into PEG-400.
3. Add appropriate quantity of ethanol and benzyl alcohol to the PEG-400-drug solution. Mix by stirring and/or vortexing, depending on the volume.
4. Weigh in an appropriate quantity surfactant.
5. Add distilled water to a total volume of 100 mL milliliters.
6. Mix and filter through a 0.2 $\mu$m nylon disposable filter unit (Nalgene) before use.
7. Store samples in the dark at temperatures equal to 25° C. or below.

The protocol for the method used to prepare a preferred parenteral formulation of the invention is given below.

772-22 Formulation Preparation:

1. Weigh 35 grams of PEG-400.
2. Dissolve appropriate amount of drug into PEG-400.
3. Add 10 grams of ethanol and 2 grams of benzyl alcohol to the PEG-400/drug solution. Mix by stirring followed by sonication for not more than 2 minutes.
4. Weigh 25 grams of CREMOPHOR EL®.
5. Add distilled sterile water to a total volume of 100 mL milliliters.
6. Mix by stirring followed by sonication for more than two minutes.
7. Filter through a 0.2 Am disposable filter unit (Nalgene).
8. Store samples in the dark at temperatures equal to 25° C. or below.

Example 3

Oral Formulations of Indolinone-Based Compounds

Oral formulations were prepared for 3-[(2,4-dimethylpyrrol-5-yl)methylene]-2-indolinone. The compositions for three formulations that enhance the solubility of the indolinone-based compound are given (Table 5).

TABLE 5

Composition of Oral Formulations:
898-52, 698-99, 980-33

| **Excipients | 898-52 Conc. % w/w | 698-99 Conc. % w/w | 980-33 Conc. % w/w |
|---|---|---|---|
| *Indolinone | 3.0 | 3.0 | 3.0 |
| GELUCIRE ® 44/14 | 70 | 0.0 | 0.0 |
| LABRASOL ® | 0.0 | 76 | 70.0 |
| Polyethylene Glycol 600 | 10 | 12 | 10 |
| Miglyol 812 | 10 | 0 | 10 |
| CREMOPHOR, EL | 10 | 12 | 10 |

*30 mg of the drug is added per gm of the vehicle
**Either USP or NF grade excipients or high purity grade were used The 898-52, 698-99, 980-33 formulations can be used for other water insoluble drugs, including other indolinone-based compounds and hydrophobic pharmaceutical agents of the invention, including quinazoline- and nitrothiazole-based compounds. For example, a drug even more hydrophobic than those disclosed herein would likely be solubilized by the formulations of the invention. The solubilization of a drug more hydrophobic than those disclosed herein could also be optimized by slightly modifying the amount of surfactant, polyglycolized lipid, oil, and/or polyoxyhydrocarbyl concentrations.

In addition, the drug concentration can be increased or decreased without modifying the contents of the formulations described herein. The formulation composition can be slightly modified to accommodate substantial increases or decreases in drug concentration by, for example, increasing or decreasing the concentration of surfactant, polyglycolized lipid, oil, and/or polyoxyhydrocarbyl compound.

Example 4
Oral Formulation Procedures

The protocol for the generic method used to prepare oral formulations of the invention is given below.
Generic Oral Preparation Procedure:
1. Melt GELUCIRE® 44/14 at 55–60° C. or heat LABRASOL® at 40° C.
2. Dissolve the other excipients into this melt.
3. Dissolve by stirring or sonicating, the hydrophobic pharmaceutical agent into this molten mixture.
4. The liquid melt can be filled into either a hard gelatin capsule or a soft gelatin capsule or used as such. The GELUCIRE® based formulation is a semi-solid at room temperature. The LABRASOL® based formulation is liquid at room temperature.
5. To obtain a solid pharmaceutical composition, the liquefied formulation (by heating if it is a semi-solid) is slowly mixed with a granulating agent until the mixture is a dry solid. This can be then filled into a hard gelatin capsule.
6. Store formulations in the dark at room temperature.

Example 5
Administration of Parenteral Formulations to Mammals Decreased Tumor Size Formulations of 3-[(2,4-dimethylpyrrol-5-yl)methylene]-2-indolinone have been administered to mice for pharmacokinetic studies. Formulations 772-22, 772-69, and 772-64 were diluted with water or in 0.45% saline, at 1:1, and 1:2 ratios respectively, before final intravenous administration. Formulations of 3-[(2,4-dimethylpyrrol-5-yl)methylene]-2-indolinone in 772-22 (50 µL, 100 µL) and 772-69 (50 µL) were also administered to tumor-bearing mice without dilution by intraperitoneal injection. The mice were administered the formulation for more than 21 days.

The formulations were efficacious—the cancer tumor sizes decreased in a large fraction of the mice tested in this study.

Example 6
Bioavailability Studies Including Administration of Oral Formulations to Mammals Several types of oral formulations, including formulations with micronized drug substances with and without surfactants, solid dispersions, lipid solutions and self emulsifying lipid vehicles like LABRASOL and GELUCIRE, have been evaluated. Among the many studied, the polyglycolized lipid-based formulations showed higher bioavailabilities. Formulation approaches like micronization, solid dispersions and solutions did not _enhance bioavailability.

Four groups of three beagle dogs were involved in the bioavailability study. All of the dogs were dosed intravenously at either 1 or 2 mg/kg. The absolute oral bioavailability of the oral formulations was determined as compared to the intravenous dose at either 1 or 2 mg/kg. Groups 1 and 4 were dosed at 2 mg/kg at the beginning of the study and their PK parameters were determined again at the end of the study. Groups 2 and 3 were dosed at 1 mg/kg. All the candidate oral formulations were dosed at 50 mg/kg in hard gelatin capsules. The formulations were melted at 60° C., filled into the capsule and stored at room temperature protected from light. The formulation is a semi-solid at room temperature. When dosed as a gavage, the formulation was melted at 60° C. and cooled to 37.5° C. before dosing.

The formulations that were tested for bioavailability are given in FIG. 1; the dosing regimens are given in FIG. 2.

One LABRASOL-based polyglycolized lipid formulation and one GELUCIRE 44/14-based polyglycolized lipid formulation had bioavailabilities in beagle dogs of 3±2% and 13±8, respectively. The LABRASOL formulation showed efficacy in the preclinical mice model for angiogenesis. At 50 mg/kg, the GELUCIRE-based formulation had about 45-fold higher bioavailability than the micronized formulation and about 4.5-fold higher bioavailability as compared to the LABRASOL-based formulation.

Factors other than dissolution are affecting bioavailability as the LABRASOL formulation in which the drug was in solution both in the formulation and on dilution (1:100, 1:10) with water pH 6.5–7, had a bioavailability lower than the semi-solid GELUCIRE-based formulation.

GELUCIRE-based formulation 898-52 provided the highest bioavailability, but there was variation between the dogs. Further testing of formulation 898-52 at 15, 50 and 100 mg/kg in fasted dogs, 50 mg/kg in fed dogs, and 50 mg/kg as a gavage (formulation melted and dosed at 37.5° C.) in fasted dogs indicated that neither food nor form (liquid or solid) had an effect on the bioavailability.

The excipients of formulation 898-52 were further tested for optimal bioavailability by: (a) substituting the polyglycolized lipid, GELUCIRE 44/14, with the higher melting, and hence slower dissolving, GELUCIRE 50/13; substituting GELUCIRE 44/14 with a mixture of LABRASOL and GELUCIRE 44/14; and substituting GELUCIRE 44/14 with a mixture of GELUCIRE 44/14 and GELUCIRE 50/13; (b) substituting the oil, Miglyol 812, with an MCM like Capmul; (c) substituting the surfactant, CREMOPHOR EL with Polysorbate; (d) increasing the surfactant concentration; (e) adding lecithin, sodium lauryl sulfate, and sodium tauroxholate; and (f) adding oleic acid. However, the optimization studies did not result in an increase in bio-availability over the original GELUCIRE formulation.

Analyses of Alanine aminotransferase and gamma glutamyl transpeptidase values were determined for all the dogs from base line up to cycle 13 (every week). The Alanine aminotransferases and Gamma glutamyl transpeptidase values did not show any significant elevation over the time span used for this study, nor any other treatment-related effect.

Example 6
Formulation Stability Studies Temperature Stability Studies

The temperature stability of formulation 898-52 (lot # 1035-049) at 25° C., 40° C. and 80° C. was tested. The two week stability profile of the formulation is shown in Table 6.

TABLE 6

Temperature Stability of the Indolinone Oral Formulation

| | % Recovery | | |
|---|---|---|---|
| Temp. | Initial | 6 days | 2 weeks |
| 25° C. | 100% | 100.49% | 100.25% |
| 40° C. | | 99.75% | 99.54% |
| 80° C. | | 98.44% | 98.00% | pH-Stability

The pH stability profile of the indolinone-based parenteral formulation, 772-69, was studied in the range of pH 2 to pH 9, at 5, 25, 40, 60 and 80° C. The formulation at pH 9 (apparent) had the maximum stability based on the degradation profile and indolinone-based compound recovery. The pH of this formulation on dilution with 0.45% saline or water ranged from 6.6–6.9. The pH-stability profile of the parenteral formulation, 772-69, at 4 weeks is given in Table 7.

TABLE 7 pH-Stability of the Parenteral Formulation

| | % INDOLINONE Remaining at Temperatures (A/A) | | | | |
|---|---|---|---|---|---|
| pH | 5° C. | 25° C. | 40° C. | 60° C. | 80° C. |
| 2 | 100.7 | 100.0 | 87.6 | 88.9 | 78.1 |
| 3 | 100.6 | 100.0 | 88.4 | 90.3 | 79.9 |
| 4 | 97.7 | 100.0 | 89.4 | 88.6 | 78.2 |
| 5 | 96.3 | 100.0 | 93.4 | 92.4 | 82.3 |
| 6 | 99.3 | 100.0 | 97.3 | 94.6 | 88.5 |
| 7 | 102.4 | 100.0 | 100.5 | 96.2 | 92.4 |
| 9 | 104.4 | 100.0 | 102.9 | 97.9 | 92.5 |

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed.

In particular, although the formulations described herein have been identified by the excipients added to the formulations, the invention is meant to also cover the final formulation formed by the combination of these excipients. Specifically, the invention includes formulations in which one to all of the added excipients undergo a reaction during formulation and are no longer present in the final formulation, or are present in modified forms.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are within the following claims.

What is claimed is:

1. A formulation comprising:
    (a) one or more hydrophobic pharmaceutical agents, wherein said agents are independently selected from the group consisting of quinazoline-, nitrothiazole-, and indolinone-based compounds;
    (b) one or more polyoxyhydrocarbyl compounds; and
    (c) one or more pharmaceutically acceptable surfactants; wherein said indolinone-based compound is an indolinone-based compound of formula VI

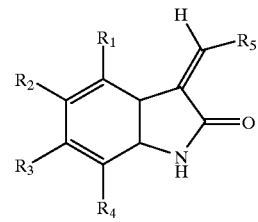

(VI)

at a concentration of about 0.1 to about 100 mg/ml;
    wherein $R_1$, $R_2$, $R_3$, $R_4$ are selected from the group consisting of hydrogen, trihalomethyl, hydroxyl, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and $R_5$ is an optionally substituted aryl or heteroaryl cyclic moiety;
    wherein at least one of said surfactants for the indolinone-based compound is PEG-400 at a concentration of about 0.01 to about 10 g/ml and at least one of said polyoxyhydrocarbyl compounds for the indolinone-based compound is ethoxylated castor oil at a concentration of about 0.01 to 10 g/ml.

2. The formulation of claim 1, wherein said hydrophobic pharmaceutical agent is a quinazoline-based compound of formula I,

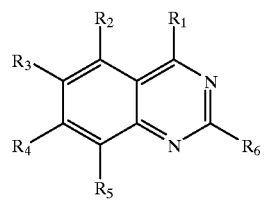

(I)

wherein $R_1$, $R_2$, $R_3$, $R_4$, $R_5$ and $R_6$ are independently selected from the group consisting of:
(i) hydrogen;
(ii) saturated or unsaturated alkyl;
(iii) an aryl optionally substituted with one, two, or three substituents independently selected from the group consisting of alkyl, alkoxy, halogen, trihalomethyl, carboxylate, nitro, and ester moieties;
(iv) an amine of formula —$NX_2X_3$, wherein $X_2$ and $X_3$ are independently selected from the group consisting of hydrogen, saturated or unsaturated alkyl, and homocyclic or heterocyclic ring moieties;
(v) halogen or trihalomethyl;
(vi) a ketone of formula —CO—$X_4$, wherein $X_4$ is selected from the group consisting of alkyl and homocyclic or heterocyclic ring moieties;
(vii) a carboxylic acid of formula —$(X_5)_n$—COOH or ester of formula —$(X_6)_n$—COO—$X_7$, wherein $X_5$, $X_6$, and $X_7$ and are independently selected from the group consisting of alkyl and homocyclic or heterocyclic ring moieties and wherein n is 0 or 1;
(viii) an alcohol of formula $(X_8)_n$—OH or an alkoxy moiety of formula —$(X_8)_n$—O—$X_9$, wherein $X_8$ and $X_9$ are independently selected from the group consisting of saturated or unsaturated alkyl and homocyclic or heterocyclic ring moieties, wherein said ring is optionally substituted with one or more substituents independently selected from the group consisting of alkyl, alkoxy, halogen, trihalomethyl, carboxylate, nitro, and ester and wherein n is 0 or 1;
(ix) an amide of formula —$NHCOX_{10}$, wherein $X_{10}$ is selected from the group consisting of alkyl, hydroxyl, and homocyclic or heterocyclic ring moieties, wherein said ring is optionally substituted with one or more substituents independently selected from the group consisting of alkyl, alkoxy, halogen, trihalomethyl, carboxylate, nitro, and ester;
(x) —$SO_2NX_{11}X_{12}$, wherein $X_{11}$ and $X_{12}$ are selected from the group consisting of hydrogen, alkyl, and homocyclic or heterocyclic ring moieties;
(xi) a homocyclic or heterocyclic ring moiety optionally substituted with one, two, or three substituents independently selected from the group consisting of alkyl, alkoxy, halogen, trihalomethyl, carboxylate, nitro, and ester moieties;
(xii) an aldehyde of formula —CO—H;
(xiii) a sulfone of formula —$SO_2$—$X_{13}$, wherein $X_{13}$ is selected from the group consisting of saturated or unsaturated alkyl and homocyclic or heterocyclic ring moieties; and (xiv) a nitro of formula —$NO_2$.

3. The formulation of claim 2, wherein said quinazoline-based compound is 4-(3-Bromophenyl)-6,7-dimethoxyquinazoline.

4. The formulation of claim 1, wherein said hydrophobic pharmaceutical agent is a nitrothiazole-based compound of formula IV,

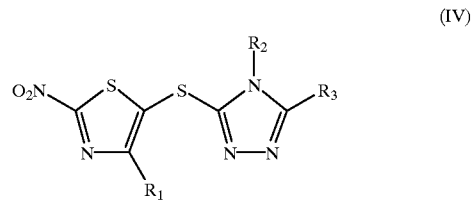

(IV)

wherein $R_1$, $R_2$, and $R_3$ are independently selected from the group consisting of
(i) hydrogen;
(ii) saturated or unsaturated alkyl;
(iii) an aryl optionally substituted with one, two, or three substituents independently selected from the group consisting of alkyl, alkoxy, halogen, trihalomethyl, carboxylate, nitro, and ester moieties;
(iv) an amine of formula —$NX_2X_3$, wherein $X_2$ and $X_3$ are independently selected from the group consisting of hydrogen, saturated or unsaturated alkyl, and homocyclic or heterocyclic ring moieties;
(v) halogen or trihalomethyl;
(vi) a ketone of formula —CO—$X_4$, wherein $X_4$ is selected from the group consisting of alkyl and homocyclic or heterocyclic ring moieties;
(vii) a carboxylic acid of formula —$(X_5)_n$—COOH or ester of formula —$(X_6)_n$—COO—$X_7$, wherein $X_5$, $X_6$, and $X_7$ and are independently selected from the group consisting of alkyl and homocyclic or heterocyclic ring moieties and wherein n is 0 or 1;
(viii) an alcohol of formula $(X_8)_n$—OH or an alkoxy moiety of formula —$(X_8)_n$—O—$X_9$, wherein $X_8$ and $X_9$ are independently selected from the group consisting of saturated or unsaturated alkyl and homocyclic or heterocyclic ring moieties, wherein said ring is optionally substituted with one or more substituents independently selected from the group consisting of alkyl, alkoxy, halogen, trihalomethyl, carboxylate, nitro, and ester and wherein n is 0 or
(ix) an amide of formula —$NHCOX_{10}$, wherein $X_{10}$ is selected from the group consisting of alkyl, hydroxyl, and homocyclic or heterocyclic ring moieties, wherein said ring is optionally substituted with one or more substituents independently selected from the group consisting of alkyl, alkoxy, halogen, trihalomethyl, carboxylate, nitro, and ester;
(x) —$SO_2NX_{11}X_{12}$, wherein $X_{11}$ and $X_{12}$ are selected from the group consisting of hydrogen, alkyl, and homocyclic or heterocyclic ring moieties;
(xi) a homocyclic or heterocyclic ring moiety optionally substituted with one, two, or three substituents independently selected from the group consisting of alkyl, alkoxy, halogen, trihalomethyl, carboxylate, nitro, and ester moieties;
(xii) an aldehyde of formula —CO—H;
(xiii) a sulfone of formula —$SO_2$—$X_{13}$, wherein $X_{13}$ is selected from the group consisting of saturated or unsaturated alkyl and homocyclic or heterocyclic ring moieties; and (xiv) a nitro of formula —NO$_2$.

5. The formulation of claim 1, wherein said hydrophobic pharmaceutical agent is a nitrothiazole-based compound of formula V,

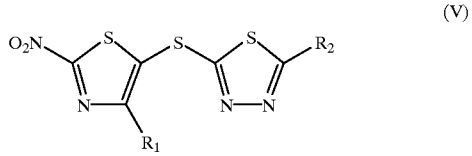

(V)

wherein R$_1$ and R$_2$ are independently selected from the group consisting of:
(i) hydrogen;
(ii) saturated or unsaturated alkyl;
(iii) an aryl optionally substituted with one, two, or three substituents independently selected from the group consisting of alkyl, alkoxy, halogen, trihalomethyl, carboxylate, nitro, and ester moieties;
(iv) an amine of formula —NX$_2$X$_3$, wherein X$_2$ and X$_3$ are independently selected from the group consisting of hydrogen, saturated or unsaturated alkyl, and homocyclic or heterocyclic ring moieties;
(v) halogen or trihalomethyl;
(vi) a ketone of formula —CO—X$_4$, wherein X$_4$ is selected from the group consisting of alkyl and homocyclic or heterocyclic ring moieties;
(vii) a carboxylic acid of formula —(X$_5$)$_n$—COOH or ester of formula —(X$_6$)$_n$—COO—X$_7$, wherein X$_5$, X$_6$, and X$_7$ and are independently selected from the group consisting of alkyl and homocyclic or heterocyclic ring moieties and wherein n is 0 or 1;
(viii) an alcohol of formula (X$_8$)$_n$—OH or an alkoxy moiety of formula —(X$_8$)$_n$—O—X$_9$, wherein X$_8$ and X$_9$ are independently selected from the group consisting of saturated or unsaturated alkyl and homocyclic or heterocyclic ring moieties, wherein said ring is optionally substituted with one or more substituents independently selected from the group consisting of alkyl, alkoxy, halogen, trihalomethyl, carboxylate, nitro, and ester and wherein n is 0 or 1;
(ix) an amide of formula —NHCOX$_{10}$, wherein X$_{10}$ is selected from the group consisting of alkyl, hydroxyl, and homocyclic or heterocyclic ring moieties, wherein said ring is optionally substituted with one or more substituents independently selected from the group consisting of alkyl, alkoxy, halogen, trihalomethyl, carboxylate, nitro, and ester;
(x) —SO$_2$NX$_{11}$X$_{12}$, wherein X$_{11}$ and X$_{12}$ are selected from the group consisting of hydrogen, alkyl, and homocyclic or heterocyclic ring moieties;
(xi) a homocyclic or heterocyclic ring moiety optionally substituted with one, two, or three substituents independently selected from the group consisting of alkyl, alkoxy, halogen, trihalomethyl, carboxylate, nitro, and ester moieties;
(xii) an aldehyde of formula —CO—H;
(xiii) a sulfone of formula —SO$_2$—X$_{13}$, wherein X$_{13}$ is selected from the group consisting of saturated or unsaturated alkyl and homocyclic or heterocyclic ring moieties; and
(xiv) a nitro of formula —NO$_2$.

6. The formulation of claim 1, wherein said one or more polyoxyhydrocarbyl compounds are water soluble polymers selected from the group consisting of: water soluble carbohydrates, water soluble carbohydrate derivatives, water soluble mixed oxyalkylene polymers, and the polymeric form of ethylene glycol.

7. The formulation of claim 6, wherein said one or more polyoxyhydrocarbyl compounds are poly(ethylene glycol) (PEG) or PEG derivatives.

8. The formulation of claim 1, wherein said one or more surfactants are one or more non-ionic surfactants.

9. The formulation of claim 1, wherein said one or more surfactants are independently selected from the group consisting of: polyoxyethylene sorbitan fatty acid esters, glyceryl monooleate, polyvinyl alcohol, ethylene oxide copolymers, polyol moieties, and sorbitan esters.

10. The formulation of claim 1, wherein said one or more surfactants are one or more ethoxylated castor oils.

11. The formulation of claim 1, wherein said formulation further comprises one or more pharmaceutically acceptable alcohols.

12. The formulation of claim 11, wherein said one or more alcohols are independently selected from the group consisting of ethanol, benzyl alcohol, propylene glycol, 2-(2-ethoxyethoxy)ethanol, and glycerol.

13. The formulation of claim 12, wherein said alcohols are independently selected from ethanol and benzyl alcohol.

14. The formulation of any of claims 1, 6–10, 11–13, wherein said formulation is effective in treating or preventing a cell proliferative disorder in a patient in need of such treatment.

15. The formulation of claim 14, wherein said formulation is administered parenterally.

16. The formulation of claim 15, wherein said patient is a mammal and said cell proliferative disorder is selected from the group consisting of cancers, blood vessel proliferative disorders, fibrotic disorders, and autoimmune disorders.

17. A method of preventing or treating a cell proliferative disorder in a patient in need of treatment comprising the following steps:
(a) diluting a parenteral formulation into a pharmaceutically acceptable solution, said parenteral formulation comprising one or more hydrophobic pharmaceutical agents, wherein said agents are independently selected from the group consisting of a quinazolin-, a nitrothiazole- and an indolinone-based compound; one or more polyoxyhydrocarbyl compounds; and one or more pharmaceutically acceptable surfactants;
wherein said indolinone-based compound is an indolinone-based compound of formula VI

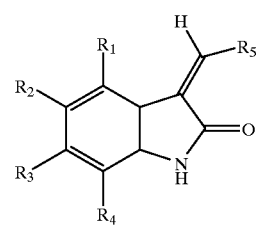

(VI)

at a concentration of about 0.1 to about 100 mg/ml;
wherein R$_1$, R$_2$, R$_3$, R$_4$ are selected from the group consisting of hydrogen, trihalomethyl, hydroxyl, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and R$_5$ is an optionally substituted aryl or heteroaryl cyclic moiety;

wherein at least one or said surfactants for the indolinone-based compound is PEG-400 at a concentration of about 0.01 to about 10 g/ml and at least one of said polyoxyhydrocarbyl compounds for the indolinone-based compound is ethoxylated castor oil at a concentration of about 0.01 to 10 g/ml; and (b) parenterally administering the diluted formulation to the patient.

18. The method of claim 17, wherein said formulation further comprises one or more pharmaceutically acceptable alcohols.

19. The method of either claim 17 or 18, wherein said patient is a mammal and said is cell proliferative disorder selected from the group consisting of cancers, blood vessel proliferative disorders, fibrotic disorders, and autoimmune disorders.

20. A formulation comprising:
(a) one or more hydrophobic pharmaceutical agents, wherein said agents are independently selected from the group consisting of quinazoline-, nitrothiazole-, and indolinone-based compounds;
(b) one or more polyoxyhydrocarbyl compounds;
(c) one or more pharmaceutically acceptable surfactants;
wherein said indolinone-based compound is an indolinone-based compound of formula VI

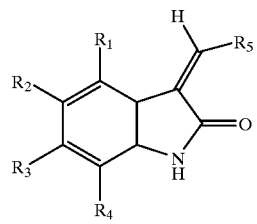

(VI)

at a concentration of about 5 mg/ml,
wherein R$_1$, R$_2$, R$_3$, R$_4$ are selected from the group consisting of hydrogen, trihalomethyl, hydroxyl, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and R$_5$ is an optionally substituted aryl or heteroaryl cyclic moiety;

wherein at least one of said surfactant for the indolinone-based compounds is PEG-400 at a concentration of about 0.35 g/ml and at least one of said polyoxyhydrocarbyl compounds for the indolinone-based compound is ethoxylated castor oil at a concentration of about 0.25 g/ml.

21. The formulation of claims 20, wherein said indolinone-based compound is selected from the group consisting of 3-[(2,4-dimethylpyrrol-5-yl)methylene]-(5-amino)-2-indolinone, 3-[(2,4-dimethylpyrrol-5-yl)methylene]-(5-chloro)-2-indolinone, 3-[(2,4-dimethylpyrrol-5 -yl)methylene]-2-indolinone, and 3-[(3-methylthiophenyl-5-yl)methylene]-(4-methyl)-2-indolinone.

22. The formulation of claim 21, wherein said indolinone-based compound is 3-[(2,4-dimethylpyrrol-5-yl)methylene]-2-indolinone.

23. A formulation comprising:
(a) an indolinone-based compound of formula VI

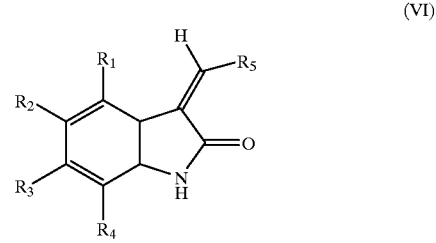

(VI)

at a concentration of about 6 mg/ml;
(b) one or more polyoxyhydrocarbyl compounds; and
(c) one or more pharmaceutically acceptable surfactants;
wherein R$_1$, R$_2$, R$_3$, R$_4$ are selected from the group consisting of hydrogen, trihalomethyl, hydroxyl, thioether, cyano, alkoxy, alkyl, amino, bromo, fluoro, chloro, iodo, mercapto, thio, cyanoamido, alkylthio, aryl, heteroaryl, carboxyl, ester, oxo, alkoxycarbonyl, alkenyl, alkoxy, nitro, alkoxyl, and amido moieties; and R$_5$ is an optionally substituted aryl or heteroaryl cyclic moiety; and R$_5$ is an optionally substituted aryl or heteroaryl cyclic moiety;

wherein at least one of said surfactant is PEG-400 at a concentration of about 0.45 g/ml and at least one of said polyoxyhydrocarbyl compounds is ethoxylated castor oil at a concentration of about 0.30 g/ml.

24. The formulation of claim 22, wherein said indolinone-based compound is selected from the group consisting of 3-[(2,4-dimethylpyrrol-5-yl)methylene]-(5-amino)-2-indolinone, 3-[(2,4-dimethylpyrrol-5-yl)methylene]-(5-chloro)-2-indolinone, 3-[(2,4-dimethylpyrrol-5-yl)methylene]-2-indolinone, and 3-[(3-methylthiophenyl-5-yl)methylene]-(4-methyl)-2-indolinone.

25. The formulation of claim 24, wherein said indolinone-based compound is 3-[2,4-dimenthylpyrrol-5-yl)methylene]-2-indolinone.

* * * * *

UNITED STATES PATENT AND TRADEMARK OFFICE
CERTIFICATE OF CORRECTION

PATENT NO.    : 6,248,771 B1                                           Page 1 of 1
DATED         : June 19, 2001
INVENTOR(S)   : Narmada Shenoy et al.

It is certified that error appears in the above-identified patent and that said Letters Patent is hereby corrected as shown below:

<u>Column 48,</u>
Line 44, claim "24" should read -- The formulation of claim 23 --.

Signed and Sealed this

Seventh Day of January, 2003

JAMES E. ROGAN
*Director of the United States Patent and Trademark Office*